US007827015B2

(12) United States Patent
McGoogan et al.

(10) Patent No.: US 7,827,015 B2
(45) Date of Patent: Nov. 2, 2010

(54) SYSTEM AND METHOD FOR OPTIMIZING ANIMAL PRODUCTION BASED ON ENVIRONMENTAL NUTRIENT INPUTS

(75) Inventors: Bruce Brim McGoogan, Plymouth, MN (US); Daniel Barziza, Belle Plaine, MN (US); Steve R. Burghardi, Eden Prairie, MN (US); David A. Cook, Coon Rapids, MN (US); Gregory L. Engelke, New Brighton, MN (US); Donald W. Giesting, Minnetonka, MN (US); Michael A. Messman, Becker, MN (US); Mark D. Newcomb, Independence, MN (US); Jennifer L. G. van de Ligt, Brooklyn Park, MN (US)

(73) Assignee: CAN Technologies, Inc., Minnetonka, MN (US)

( * ) Notice: Subject to any disclaimer, the term of this patent is extended or adjusted under 35 U.S.C. 154(b) by 681 days.

(21) Appl. No.: 11/191,255

(22) Filed: Jul. 27, 2005

(65) Prior Publication Data

US 2006/0041408 A1    Feb. 23, 2006

Related U.S. Application Data

(63) Continuation-in-part of application No. 10/902,504, filed on Jul. 29, 2004.

(51) Int. Cl.
*G06G 7/58* (2006.01)
(52) U.S. Cl. .............................. 703/11; 703/2; 702/19; 700/28; 706/11; 706/19
(58) Field of Classification Search ....................... None
See application file for complete search history.

(56) References Cited

U.S. PATENT DOCUMENTS

| 4,463,706 A | 8/1984 | Meister et al. |
|---|---|---|
| 4,493,290 A | 1/1985 | Gibbard |
| 4,498,424 A | 2/1985 | Leuschner |
| 4,517,923 A | 5/1985 | Palmer |
| 4,532,892 A | 8/1985 | Kuzara |
| 4,589,372 A | 5/1986 | Smith |

(Continued)

FOREIGN PATENT DOCUMENTS

EP        0 715 806 A1    6/1996

(Continued)

OTHER PUBLICATIONS

Tedeschi et al., "Whole-herd optimization with the Cornell Net Carbohydrate and Protein System. I. Predicting feed biological values for diet optimization with linear programming", 2000, Journal of Dairy Science, vol. 83, pp. 2139-2148).*

(Continued)

*Primary Examiner*—Carolyn L. Smith

(57) ABSTRACT

A system for generating an animal feed formulation based on environmental nutrient inputs. The system comprises a simulator engine configured to generate a set of animal requirements in view of environmental nutrients received by an animal based on characteristics of the animal and a formulator engine configured to receive the set of animal requirements and generate an optimized animal feed formulation based on the animal requirements.

23 Claims, 5 Drawing Sheets

U.S. PATENT DOCUMENTS

| | | | |
|---|---|---|---|
| 4,712,511 | A | 12/1987 | Zamzow et al. |
| 4,729,894 | A | 3/1988 | Teeter |
| 5,105,767 | A | 4/1992 | Gordon et al. |
| 5,174,244 | A | 12/1992 | Gaalswyk |
| 5,309,864 | A | 5/1994 | Harmsen et al. |
| 5,355,833 | A | 10/1994 | Legrain |
| 5,374,524 | A | 12/1994 | Miller |
| 5,474,085 | A | 12/1995 | Hurnik et al. |
| 5,478,989 | A | 12/1995 | Shepley |
| 5,579,719 | A | 12/1996 | Hoff et al. |
| 5,595,444 | A | 1/1997 | Tong et al. |
| 5,636,118 | A | 6/1997 | Brewster et al. |
| 5,668,718 | A | 9/1997 | Liu et al. |
| 5,673,647 | A | 10/1997 | Pratt |
| 5,700,590 | A | 12/1997 | Masor et al. |
| 5,816,191 | A | 10/1998 | Beaudoin et al. |
| 5,843,498 | A | 12/1998 | Takahashi |
| 5,878,402 | A | 3/1999 | Brewster et al. |
| 5,901,660 | A | 5/1999 | Stein |
| 6,076,043 | A | 6/2000 | Liu |
| 6,082,304 | A | 7/2000 | Crain |
| 6,115,692 | A | 9/2000 | Liu et al. |
| 6,135,055 | A | 10/2000 | Pratt |
| 6,314,909 | B1 | 11/2001 | Horwood |
| 6,394,963 | B1 | 5/2002 | Blazey et al. |
| 6,556,948 | B1 | 4/2003 | McKenna |
| 6,658,308 | B1 | 12/2003 | van de Ligt et al. |
| 6,681,717 | B2 | 1/2004 | Burghardi et al. |
| 6,805,074 | B2 | 10/2004 | Newcomb et al. |
| 6,868,804 | B1 | 3/2005 | Huisma et al. |
| 6,895,893 | B2 | 5/2005 | Larsen |
| 2002/0082486 | A1 | 6/2002 | Lavery et al. |
| 2002/0120402 | A1* | 8/2002 | Burghardi et al. ............ 702/19 |
| 2004/0098209 | A1 | 5/2004 | Burghardi et al. |

FOREIGN PATENT DOCUMENTS

| | | |
|---|---|---|
| HU | 209 360 A | 5/1994 |
| WO | WO 00/41575 A1 | 7/2000 |
| WO | WO 01/54043 A1 | 7/2001 |
| WO | WO 01/89285 A2 | 11/2001 |
| WO | WO 02/02822 A2 | 1/2002 |
| WO | WO 02/47473 A2 | 6/2002 |

OTHER PUBLICATIONS

Black et al., "Simulation of energy and amino acid utilisation in the pig" *Research and Development in Agriculture*, vol. 3, No. 3, 1986 (pp. 121-145).

Chavas et al., "Modeling Dynamic Agricultural Production Response: The Case of Swine Production," *Amer. J. Agr. Econ.*, vol. 67, No. 3, Aug. 1985 (pp. 636-646).

Derwent Abstract of EP 0715 806 A1; Accension No. 1996-260514 (2 pp.).

Derwent Abstract of SU 843 889; Accension No. 1982-E5977E (1 p.).

Devresse, "Nutrient Levels in Some Commercial Shrimp Feeds and Feed Ingredients of Asia and Latin America—A Comparative Analysis," Inve Aquaculture N.V.Oeverstraat, 7 B-9200 Belgium, available at least by Aug. 6, 2001 (pp. 49-70).

D'Mello, "Utilization of dietary purines and pyrimidines by non-ruminant animals," *Proc. Nutr. Soc.*, vol. 41, 1982 (pp. 301-308).

Emmans. "The growth of turkeys" (pp. 135-166)., Recent Adv. in Turkey Science, 1989.

Fisher et al., "A Model for the Description and Prediction of the Response of Laying Hens to Amino Acid Intake," *Br. Poult. Sci.*, vol. 14, 1973 (pp. 469-484).

Howie, "Condensed Porcine Solubles® suitable source of energy, protein for swine," Feedstuffs, Oct. 26, 1998, The Miller Publishing Company, a company of Rural Press Ltd. (2 pp.).

Hungarian Patent Office, Novelty Search Report for Hungarian Application No. P0302586, Mar. 25, 2004 (1 p.).

JP 9028678, "Apparatus for Determining Stress", Partial English Translation of Abstract, Publication Date Feb. 4, 1997, available at esp@cenet database (1 p.).

JP 8052116, "Diagnostic Support System by Skin Temperature of Horse", Partial English Translation of Abstract, Publication Date Feb. 27, 1996, available at esp@cenet database (1 p.).

Karasawa et al., "Effect of Dietary RNA on Growth and Food Intake of Young Chicks", *Jpn. Poult. Sci.*, vol. 27, vol. 3, 1990 (pp. 165-172).

Kilpatrick et al., "A predictive model for beef cattle growth and carcass composition", *Agricultural Systems*, vol. 61, 1999 (pp. 95-107).

Kubota et al., "Adverse Effects of Low Concentrations of Dietary RNA Addition on the Growth, Food Intake and Kidney Weight of Young Chickens", *British Poultry Science*, vol. 35 1994 (pp. 585-588).

"Orotate supplementation for starter diet for swine", vol. 61, 1995, Nutri-Quest, Inc., 1400 Elbridge Payne Road, Chesterfield, MO 63017 (2 pp.).

Schematic representation of computer system commercially used by Cargill, Inc. prior to Jun. 2001 (Figures 1-3 from WO 02/47473) (3 pp.).

Schematic representation of computer system commercially used by Cargill, Inc. prior to Dec. 1999 (1 p.).

Talpaz et al., "Dynamic Optimization Model for Feeding of Broilers", *Agricultural Systems*, vol. 20, 1986 (pp. 121-132).

"What's all this noise about nucleotides?", *Feeding Times*, vol. 6, No. 2, 2001 (pp. 18-19).

* cited by examiner

SYSTEM AND METHOD FOR OPTIMIZING ANIMAL PRODUCTION BASED ON ENVIRONMENTAL NUTRIENT INPUTS

CROSS REFERENCE TO RELATED APPLICATIONS

This application is a continuation-in-part of U.S. application Ser. No. 10/902,504, filed Jul. 29, 2004, the entire content of which is hereby incorporated by reference.

BACKGROUND

The present invention relates generally to the field of systems for and methods of animal production. More particularly, the present invention relates to systems for and methods of optimizing animal production based on environmental nutrient inputs to an animal production system.

An animal production system may include any type of system or operation utilized in producing animals or animal based products. Examples may include farms, ranches, aquaculture farms, animal breeding facilities, etc. Animal production facilities may vary widely in scale, type of animal, location, production purpose, etc. However, almost all animal production facilities can benefit from identifying and implementing improvements to production efficiency. Improvements to production efficiency can include anything that results in increased production results, improved proportional output of desired products versus less desirable products (e.g. lean vs. fat), and/or decreased production costs.

A producer (i.e. a farmer, rancher, aquaculture specialist, etc.) generally benefits from maximizing the amount or quality of the product produced by an animal (e.g. gallons of milk, pounds of meat, quality of meat, amount of eggs, nutritional content of eggs produced, amount of work, hair/coat appearance/health status, etc.) while reducing the cost for the inputs associated with that production. Exemplary inputs may include animal feed, animal facilities, animal production equipment, labor, medicine, etc.

Animal feeds are compositions of a large variety of raw materials or ingredients. The ingredients can be selected to optimize the amount of any given nutrient or combination of nutrients in an animal feed product based upon the nutrient composition of the ingredient mixture used.

The nutritional composition of any one feed ingredient can be used in combination with the nutritional composition of every other ingredient in the feed to produce an animal feed that maximizes or minimizes an evaluation criteria. One example of an evaluation criteria is the growth and production rate of the animal in the shortest amount of time. Other examples of evaluation criteria can include, but are not limited to, a work rate for an animal, an appearance of an animal, a health state of an animal, etc. Animal feed producers have recognized that certain nutritional compositions help animals to meet or exceed evaluation criteria better than other nutritional compositions. For example, a particular cow feed composition can be made that will deliver an improved balance of essential amino acids post ruminally. This has been shown to have the effect of increasing the cow's milk production.

Similarly, animal feed producers have recognized that certain environmental nutrient inputs can affect the nutrients that are ingested by the animal which has an effect on the animals in meeting or exceeding evaluation criteria. For example, dairy animals are often allowed to roam in a pasture where they are likely to consume grasses growing in the pasture. This consumption reduces the animal's consumption of a customized animal feed that will optimize growth by substituting for a portion of the maximal dry matter intake the animal may consume or altering an animal's metabolism of the customized animal feed. Alternatively, the pasture may include levels of other substances that may have a toxic effect either alone or when combined with the nutrients in a customized animal feed.

What is needed is a method and system for maximizing nutritional criteria satisfaction in view of environmental nutrient inputs to an animal's nutrient intake. Further, there is a need for a system and method to create a customized animal feed formulated to satisfy some requirement in view of the environmental nutrient inputs. What is yet further needed is such a system and method configured to generate one or more modification recommendation to modify the environmental nutrient inputs in view of the customized animal feed.

SUMMARY

One embodiment of the invention relates to a system for generating an animal feed formulation based on environmental nutrient inputs. The system comprises a simulator engine configured to generate a set of animal requirements in view of environmental nutrients received by an animal based on characteristics of the animal and a formulator engine configured to receive the set of animal requirements and generate an optimized animal feed formulation based on the animal requirements.

Another embodiment of the invention relates to a method for generating an animal feed formulation based on environmental nutrient inputs. The method includes receiving a listing of environmental nutrient inputs, generating a projection of the consumption of the environmental nutrient inputs by an animal, determining a set of animal nutritional requirements in view of the consumption of the environmental nutrient inputs by the animal based on the characteristics of the animal, and generating an optimized animal feed formulation based on the animal requirements.

Yet another embodiment of the invention relates to a system for generating an animal feed formulation. The system includes a simulator engine configured to receive a plurality of animal information inputs and generate animal requirements based on the animal information inputs. The animal information inputs include a listing of environmental ingredients available to the animal, wherein at least one of the animal information inputs is designated as a variable input. The system further includes a formulator engine configured to receive a plurality of animal feed ingredient inputs and generate an animal feed formulation composed of the animal feed ingredients based on the animal requirements and projected consumption of the environmental ingredients by the animal and an enterprise supervisor engine configured to optimize the animal feed formulation according to at least one optimization criteria and further configured to generate an optimized value for the at least one variable input based on the at least one optimization criteria.

Other features and advantages of the present invention will become apparent to those skilled in the art from the following detailed description and accompanying drawings. It should be understood, however, that the detailed description and specific examples, while indicating preferred embodiments of the present invention, are given by way of illustration and not limitation. Many modifications and changes within the scope of the present invention may be made without departing from the spirit thereof, and the invention includes all such modifications.

BRIEF DESCRIPTION OF THE DRAWINGS

The exemplary embodiments will hereafter be described with reference to the accompanying drawings, wherein like numerals depict like elements, and.

DETAILED DESCRIPTION

In the following description, for the purposes of explanation, numerous specific details are set forth in order to provide a thorough understanding of the present invention. It will be evident to one skilled in the art, however, that the exemplary embodiments may be practiced without these specific details. In other instances, structures and devices are shown in diagram form in order to facilitate description of the exemplary embodiments.

In at least one exemplary embodiment illustrated below, a computer system is described which has a central processing unit (CPU) that executes sequences of instructions contained in a memory. More specifically, execution of the sequences of instructions causes the CPU to perform steps, which are described below. The instructions may be loaded into a random access memory (RAM) for execution by the CPU from a read-only memory (ROM), a mass storage device, or some other persistent storage. In other embodiments, multiple workstations, databases, processes, or computers can be utilized. In yet other embodiments, hardwired circuitry may be used in place of, or in combination with, software instructions to implement the functions described. Thus, the embodiments described herein are not limited to any particular source for the instructions executed by the computer system.

Figure 1:
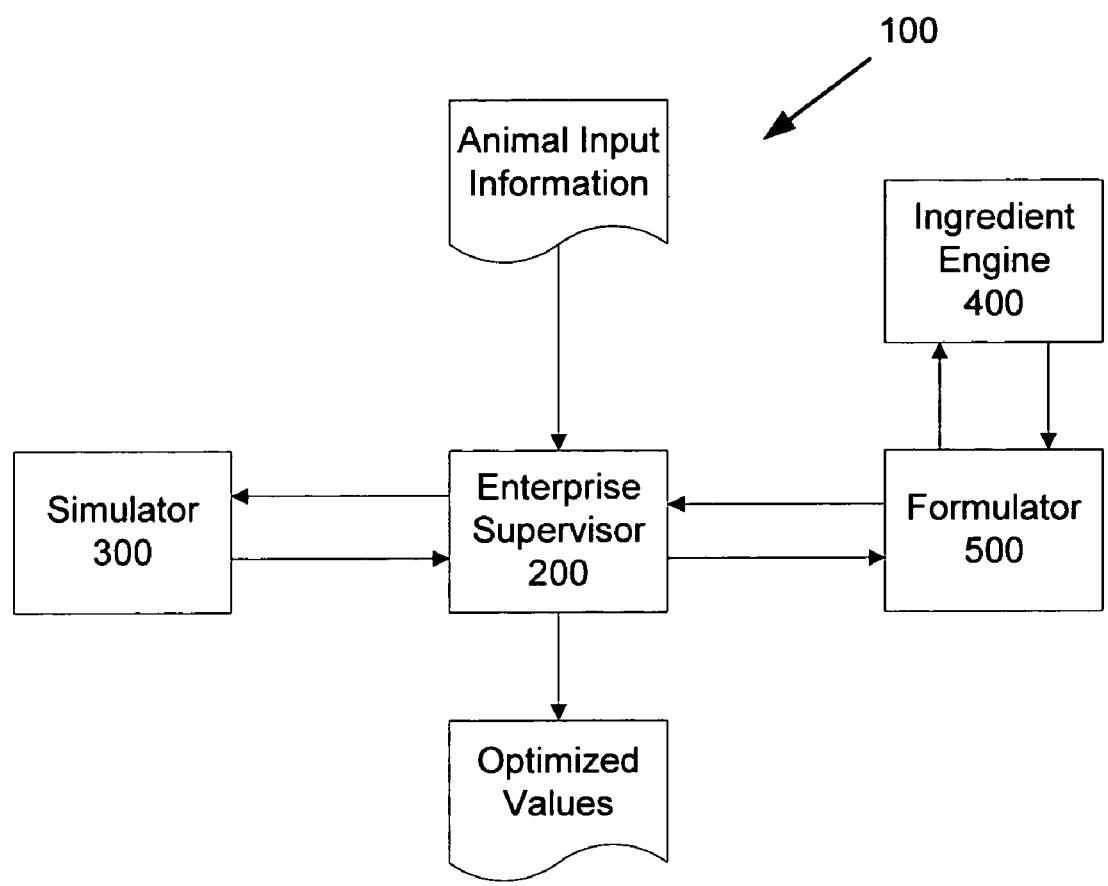
FIG. 1 is a general block diagram illustrating an animal production optimization system, according to an exemplary embodiment.

Referring now to FIG. 1, a general block diagram is shown illustrating an animal production optimization system 100, according to an exemplary embodiment. System 100 includes an enterprise supervisor 200, a simulator 300, an ingredient engine 400, and a formulator 500.

System 100 may be implemented utilizing a single or multiple computing systems. For example, where system 100 is implemented using a single computing system, each of enterprise supervisor 200, simulator 300, ingredient engine 400, and formulator 500 may be implemented on the computing system as computer programs, discrete processors, subsystems, etc. Alternatively, where system 100 is implemented using multiple computers, each of enterprise supervisor 200, simulator 300, ingredient engine 400, and formulator 500 may be implemented using a separate computing system. Each separate computing system may further include hardware configured for communicating with the other components of system 100 over a network. According to yet another embodiment, system 100 may be implemented as a combination of single computing systems implementing multiple processes and distributed systems.

System 100 is configured to receive animal information input including at least one variable input and analyze the received information to determine whether variation in one or more of the variable inputs will increase animal productivity or satisfy some other optimization criteria. Animal productivity may be a relative measure of the amount, type, or quality of output an animal produces relative to the expense associated with that production. Animal information input can include any type of information associated with an animal production system. For example, animal information input may be associated with a specific animal or group of animals or type of animals, an animal's environment, an economy related to the animal production, etc. Animal productivity may further be configured to include positive and negative outputs associated with the production. For example, animal productivity may be configured to represent harmful gaseous emissions as an expense (based on either financial costs associated with clean up or the negative impact on the environment), reducing the overall productivity.

Information associated with a specific animal or a group or type of animals may include, but is not limited to, a species, a state, an age, a production level, a job, a size (e.g. current, target, variability around, etc.), a morphology (e.g. intestinal), a body mass composition, an appearance, a genotype, a composition of output, a collection of microbial information, health status, a color, etc. The information associated with a specific animal may be any type of information relevant for determining the productivity of the animal.

Species information can include a designation of any type or class of animals such as domestic livestock, wild game, pets, aquatic species, humans, or any other type of biological organism. Livestock may include, but is not limited to, swine, dairy, beef, equine, sheep, goats, and poultry. Wild game may include, but is not limited to, ruminants, such as deer, elk, bison, etc., game birds, zoo animals, etc. Pets may include, but are not limited to, dogs; cats, birds, rodents, fish, lizards, etc. Aquatic species may include, but are not limited to, shrimp, fish (production), frogs, alligators, turtles, crabs, eels, crayfish, etc. and include those species grown for productive purposes (e.g., food products).

Animal state may include any reference or classification of animals that may affect the input requirement or production outputs for an animal. Examples may include, but are not limited to, a reproductive state, including gestation and egg laying, a lactation state, a health state or stress level, a maintenance state, an obese state, an underfed or restricted-fed state, a molting state, a seasonal-based state, a compensatory growth, repair or recovery state, a nutritional state, a working or athletic or competitive state, etc. Animal health states or stress level may further include multiple sub-states such as normal, compromised, post-traumatic (e.g. wean, mixing with new pen mates, sale, injury, transition to lactation, etc.), chronic illness, acute illness, immune response, an environmental stress, etc.

Animal age may include an actual age or a physiological state associated with an age. Examples of physiologic states may include a developmental state, a reproductive state including cycles, such as stage and number of pregnancies, a lactation state, a growth state, a maintenance state, an adolescent state, a geriatric state, etc.

Animal job may include a physiologic state as described above, such as gestation, lactation, growth, egg production, etc. Animal job may further include the animal's daily routine or actual job, especially with reference to canine and equines. Animal job may also include an animal movement allowance, such as whether the animal is generally confined versus allowed free movement in a pasture, or, for an aquatic animal, the different water flows the aquatic animal experiences, etc.

Animal size may include the actual weight, height, length, circumference, body mass index, mouth gape, etc. of the animal. The animal size may further include recent changes in animal size, such as whether the animal is experiencing weight loss, weight gain, growth in height or length, changes in circumference, etc.

Animal morphology includes a body shape exhibited by an animal. For example, a body shape may include a long body, a short body, a roundish body, etc. Animal morphology may further include distinct measurement of internal organ tissue changes such as the length of intestinal villi, depth of intestinal crypts, and/or other organ sizes or shapes.

Animal body mass composition may include a variety of composition information such as a fatty acid profile, a vitamin E status, a degree of pigmentation, a predicted body mass composition, etc. The body mass composition generally is a representation of the percentage or amount of any particular component of body mass, such as lean muscle, water, fat, etc. The body mass composition may further include separate representations composition for individual body parts/sections. For example, body mass composition may include edible component compositions such as fillet yield, breast meat yield, tail meat yield, etc.

Animal appearance may include any measure or representation of an animal appearance. Examples can include the glossiness of an animal's coat, an animal's pigmentation, muscle tone, feather quality, feather cover, etc.

Animal genotype may include any representation of all or part of the genetic constitution of an individual or group. For example, an animal genotype may include DNA markers associated with specific traits, sequencing specific segments of DNA, etc. For example, the genotype may define the genetic capability to grow lean tissue at a specific rate or to deposit intramuscular fat for enhanced leanness or marbling, respectively. Additionally, genotype may be defined by phenotypic expression of traits linked to genotypic capacity such as the innate capacity for milk production, protein accretion, work, etc.

Composition of output may include the composition of a product produced by an animal. For example, the composition of output may include the nutrient levels found in eggs produced by poultry or milk produced by dairy cows, the amount, distribution, and/or composition of fat in meat products, a flavor and texture profile for a meat product, interrelationship between compositional part ratios, etc.

Microbial and/or enzyme information may include current microbial populations within an animal or within an animal's environment. The microbial and/or enzyme information may include measures of the quantity or proportion of gram positive or negative species or other classifications such as aerobes, anaerobes, *salmonella* species, *E. coli* strains, etc. Enzyme information may include the current content, quantity and/or composition of any enzyme sub-type or activation state, such as protease, amylase, and/or lipase, produced by the pancreas, produced within the gastrointestinal tract, enzymes produced by a microbial population, a microbial community relationship at various ages, etc. Microbial and/or enzyme information may further include information about potential nutritional biomass represented by the current and/or a suggested microbial community that may be used as a feed source for some species (e.g., ruminants, aquatic species, etc.). The microbial and/or enzymatic environment may be monitored using any of a variety of techniques that are known in the art, such as cpn60, other molecular microbiological methods, and in vitro simulation of animal systems or subsystems.

Animal information input associated with an animal or group of animals' environment may include, but is not limited to, factors related specifically to the environment, factors related to the animal production facility, etc. Animal environment may include any factors not associated with the animal that have an effect on the productivity of the animal or group of animals.

Examples of animal information input related to the environment may include ambient temperature, wind speed or draft, photoperiod or the amount of daylight exposure, light intensity, light wave length, light cycle, acclimation, seasonal effects, humidity, air quality, water quality, water flow rate, water salinity, water hardness, water alkalinity, water acidity, aeration rate, system substrate, filter surface area, filtration load capacity, ammonia levels, geographic location, mud score, etc. The environmental information may further include detailed information regarding the system containing the animal or animals, such as system size (e.g. the size in square meters, size in square centimeters, hectares, acres, volume, etc.), system type (pens, cages, etc.), system preparation such as using liming, discing, etc., aeration rate, system type, etc. Although some environmental factors are beyond the control of a producer, the factors can usually be modified or regulated by the producer. For example, the producer may reduce draft by closing vents, raise ambient temperature by including heaters or even relocating or moving certain animal production operations to a better climate for increasing productivity. According to another example, an aqua producer may modify nutrient inputs to an aquatic environment by altering a feed design or feeding program for the animals in the environment. According to an exemplary embodiment, animal information input related to the environment may be generated automatically using an environmental appraisal system (EAS) to calculate a thermal impact estimate for an animal and to provide measurements for the animal's current environment.

Examples of animal information input related to a production facility may include animal density, animal population interaction, feeder type, feeder system, feeder timing and distribution, pathogen loads, bedding type, type of confinement, facility type, feathering, lighting intensity, lighting time patterns, time in holding pen, time away from feed, etc. Animal information input for a production facility may be modified by a producer to increase productivity or address other production goals. For example, a producer may build additional facilities to reduce population density, obtain additional or different types of feeding systems, modify the type of confinement, etc.

Animal information input associated with economic factors may include, but is not limited to, animal market information. Animal market information may include, but is not limited to, historical, current and/or projected prices for outputs, market timing information, geographic market information, product market type (e.g., live or carcass-based), etc.

Animal information inputs may further include any of a variety of inputs that are not easily classifiable into a discrete group. Examples may include an animal expected output (e.g., milk yield, product composition, body composition, etc.), a user defined requirement, a risk tolerance, an animal mixing (e.g., mixing different animals), variations with an animal grouping, etc., buyer or market requirements (e.g. Angus beef, Parma hams, milk for particular cheeses, a grade for tuna, etc.), expected and/or targeted growth curves, survival rates, expected harvest dates, etc.

The above described animal information input may include information that is directly received from a user or operator through a user interface, as will be described below with reference to FIG. 2. Alternatively, the animal information input or some part of the input may be retrieved from a database or other information source.

Further, some of the inputs may be dependent inputs that are calculated based on one or more other inputs or values. For example, an animal's stress level may be determined or estimated based on population density, recent weight loss, ambient temperature, metabolic indicators such as glucose or cortisol levels, etc. Each calculated value may include an option enabling a user to manually override the calculated value. Similarly, immune states may vary according to age, nutrient types and input level, microbial challenges, maternal passive immunity provision, etc.

Yet further, each animal information input may include a variety of information associated with that input. For example, each animal information input may include one or more subfields based on the content of the animal information input. For example, where an indication is provided that an animal is in a stressed state, subfields may be received indicating the nature and severity of the stress.

According to an exemplary embodiment, the animal information input includes a capability to designate any of the animal information inputs as a variable input. A variable input may be any input that a user has the ability to modify or control. For example, a user may designate ambient temperature as a variable input based on the ability to modify the ambient temperature through a variety of methods such as heating, cooling, venting, etc. According to an alternative embodiment, system 100 may be configured to automatically recommend specific animal information inputs as variable inputs based on their effect on productivity or satisfying the optimization criteria, as will be further discussed below with reference to FIG. 2.

Designation of a variable input may require submission of additional information, such as a cost and/or benefit of variation of the variable input, recommended degrees of variation for optimization testing, etc. Alternatively, the additional information may be stored and retrievable from within system 100 or an associated database.

The animal information inputs may further include target values as well as current values. A target value may include a desirable level for animal productivity or some aspect of animal productivity. For example, a producer may wish to target a specific nutrient level for eggs produced by poultry. Therefore, the producer may enter current nutrient levels for eggs currently being produced as well as target nutrient values for the eggs. According to another example, a current size breakdown for shrimp in a pond versus a potential size breakdown. The target values and current values may be utilized by system 100 to make changes in an animal feed formulation or to make changes to variable inputs as will be described further below. Further, the target values may be viewed as equality constraints and/or inequality constraints for the optimization problem.

Table 1 below lists exemplary animal information inputs that may be provided as inputs to animal production optimization system 100. This listing of potential animal information inputs is exemplary and not exclusive. According to an exemplary embodiment, any one or more of the listed animal information inputs can be designated as a variable input.

TABLE 1

| General Characteristics | | |
|---|---|---|
| Impact of the ration on the greater environment: | Quantity and/or composition (e.g. nitrogen, phosphorus, etc.) of manure or litter per animal<br>Quantity and/or quality of odor from facility | Quantity and/or composition of urine |

| Swine Characteristics | | |
|---|---|---|
| Sow reproductive performance | | |
| No. of pigs born | No. of pigs born alive | No. of pigs weaned |
| Piglets birth weight | Uniformity of baby pigs | Mortality of baby pigs |
| Piglets weaning weight | Sow body condition score | Sow lactation back fat loss |
| Sow lactation weight loss | Interval weaning to estrus | Sow longevity |
| | Working boar | |
| Body condition score | Working frequency | Semen quality |
| Finisher | | |
| Average daily gain | Average daily lean gain | Average daily feed intake per weight gain |
| Average daily feed intake per lean gain | Feed wastage | Feed form |
| Mortality | Days to market | Feed cost per kg gain |
| Feed cost per kg lean gain | Medication usage per pig | Dressing percentage |
| Lean percentage | Back fat thickness | Fatty acid composition |
| Evaluation Criteria for Environment | | |
| Thermal environment (Draft, Floor type, Bedding, Insulation) | Air quality (Dust, Humidity, Ammonia, Carbon dioxide, etc) | Pig/pen |
| Pig density | Health condition | Feeder type |
| Pigs/feeder hole | Water quality and quantity | Immune status |

TABLE 1-continued

| Evaluation Criteria for appearance | | |
|---|---|---|
| Hair coat condition | Skin color | Ham shape |
| Body shape and length | | |

| Evaluation Criteria for meat/fat quality | | |
|---|---|---|
| Meat and fat color | Iodine value | Fatty acid profile |
| PSE | Juiciness | Flavor |
| Tenderness | Marbling score | Water holding capacity |

| Evaluation Criteria for Health |||
|---|---|---|
| Suckling piglets | | |
| Eye condition (dry and dirty or bright and vital eyes) | Skin condition (elastic or dry) and color (pink or pale) | Hair condition (dense or coarse) |
| Dirtiness of around anus | Breathe with open mouth | Belly condition |

| Finisher | | |
|---|---|---|
| Respiratory disease | Body temperature | Cannibalism (tail, ear, belly biting) |
| Skin and hair condition (mange and parasites) | Stool condition | Swollen knee and ankle joint |
| Dirtiness of around eyes | Nose condition | Respiratory sound (Difficulties in breathing) |
| Activity | Microbial profile or levels | |

| Sows | | |
|---|---|---|
| MMA (Mastitis, Metritis, Agaclactia) | Stool condition (constipation) | Abortion and stillbirth |
| Wet belly | Body shaking | Vaginal and uterine prolapse |
| Body condition score | Interval weaning to estrus | Feed intake (sick sows eat less) |
| Leg problem | Body temperature | |

| Dairy Characteristics | | |
|---|---|---|

| Cow reproductive performance | | |
|---|---|---|
| Breeding per conception | Live birth | Days to first estrous |
| Calf birth weight | Days open | Days to cleaning |
| Calf weaning weight | Cow body condition score | MUN and BUN |
| Cow body reserve change | Calving interval | Blood hormones progesterone and estrogen |

| Lactation | | |
|---|---|---|
| Milk per day | Body fatty acid loss or gain | Average daily feed intake per kg milk |
| | Feed wastage | Feed form |
| Mortality | Lactation length | Feed cost per kg milk |
| Milk per year and lifetime milk | Morbidity | Body amino acid loss or gain |
| Fatty acid composition of milk (CLA, EPA and DHA, 18:2 to 18:3 ratio of milk) | | |

| Evaluation Criteria for Environment | | |
|---|---|---|
| Thermal environment (Draft, Floor type, Bedding, Insulation) | Air quality (Dust, Humidity, Ammonia, Carbon dioxide, etc) | Blood cortisol, NEFA |
| Animal density | Health condition | Feed presentation method |
| Cows per bunk or waterer space | Water quality and quantity | Cow care and comfort score card |

| Evaluation Criteria for appearance | | |
|---|---|---|
| Hair coat condition | Skin color | Body condition score |
| Body shape and length | Color of mucus membrane | Appearance of eyes and ears |

| Evaluation Criteria for milk quality | | |
|---|---|---|
| Milk color | Milk protein composition | Milk fat yield |
| Milk flavor | Milk lactose | Milk protein yield |
| Milk fatty acid composition | Total milk solids | |

TABLE 1-continued

Evaluation Criteria for Health

Calves

| | | |
|---|---|---|
| Eye condition (dry and dirty or bright and vital eyes) | Skin condition (elastic or dry) and color (pink or pale) | Hair condition (dense or coarse) |
| Dirtiness of around anus | Breathe with open mouth | Belly condition |
| Body Temperature | | |

Heifers

| | | |
|---|---|---|
| Respiratory disease | Body temperature | |
| Skin and hair condition (mange and parasites) | Stool condition | Swollen knee and ankle joint |
| Dirtiness of around eyes | Nose condition | Respiratory sound (Difficulties in breathing) |
| Activity | | |

Cows

| | | |
|---|---|---|
| Mastitis, Metritis | Stool condition (constipation) manure screener | Abortion and stillbirth |
| Blood measures EX: cortisol, NEFA, BHBA, alkaline phosphitase, progesterone estrogen bun | Body shaking | Vaginal and uterine prolapse |
| Body condition score | Calving interval | Feed intake (sick cows eat less) |
| Leg problem | Body temperature | Milk urea nitrogen |

Companion Animal and Equine Characteristics

| | | |
|---|---|---|
| Hair coat shine | Hair coat-fullness | Skin scale/flake level |
| Fecal consistency | Gas production | Breath |
| Immune status | Antioxidant status | Body condition (thin, normal, obese) |
| skeletal growth rate | Endurance | Digestive health status |
| Circulatory health status | Hoof quality | Hair quality |
| Body fluid status | Workload (NRC specifies light, medium and heavy workloads) | |

Characteristics to optimize for athlete animals:

| | | |
|---|---|---|
| Speed | Sprint | Muscular glycogen spare |
| Muscular glycogen recovery | Decrease recovery time after exercise | Endurance |
| Body condition | | |

Health and Welfare of the Animal:

| | | |
|---|---|---|
| Welfare and behavior (calmer or energetic diet): | Relationship between NDF/starch or forage/grain | Dry matter intake |
| | Long fiber intake | Electrolytes |
| General health status: | Low allergenicity | Digestive health |
| | Improving immunologic status | Increasing antioxidant status |
| | Minimize digestive upset | |
| Immunologic status | | |

Beef Characteristics

Cow reproductive performance

| | | |
|---|---|---|
| Conception rate | Weaning rate | Calf birth weight |
| Calf mortality | Calf weaning weight | Cow body condition score |
| Interval weaning to estrus | Calving interval | |

Bulls

| | | |
|---|---|---|
| Body condition score | Breeding Soundness | |

Growing and Finishing

| | | |
|---|---|---|
| Average daily lean gain | Average daily feed intake per gain | Feed cost per unit gain |
| Feed cost per unit lean gain | Stocking Rate | |

Evaluation Criteria for Environment

| | | |
|---|---|---|
| Air quality | Nutrient excretion | |

TABLE 1-continued

| Evaluation Criteria for appearance | | |
|---|---|---|
| Hair coat condition | Height | Height/weight ratio |

| Evaluation Criteria for meat/fat quality | | |
|---|---|---|
| Meat and fat color | Fatty acid profile | Juiciness |
| Flavor | Tenderness | Marbling score |
| Dressing percentage | Red meat yield | Muscle pH |
| Intra muscular fat | Antioxidant status | |

| Evaluation Criteria for Health | | |
|---|---|---|
| Mortality | Medication cost | Morbidity |

Poultry Characteristics

| Egg and reproduction | | |
|---|---|---|
| Egg number | Fertility | Hatchability |
| Egg weight | Egg mass | Egg internal quality (Haugh Units) |
| Egg yolk color | Eggshell quality | Egg bacteriological content (Salmonella-fee) |
| Fertile eggs breakout analysis | | |

| Performance | | |
|---|---|---|
| Average daily gain | Average daily feed intake | Feed conversion |
| Mortality | Occurrences of Leg problem | Feed cost per kg gain live weight |
| Feed cost per dozen eggs | Yield of Eviscerated carcass | Yield of body parts (breast, thigh, back etc.) |
| Flock Uniformity | Feed consumption | |

| Environment | | |
|---|---|---|
| Temperature | Air quality (Dust, Humidity, Ammonia, Carbon dioxide, etc) | Bird density |
| Feeder space | Lighting program | Water quality and quantity |
| Litter quality (Wet droppings) | Biosecurity | Immune Status |
| Microbial profile or levels | | |

| Evaluation Criteria for appearance | | |
|---|---|---|
| Feathering score | Skin color | Skin scratching score |
| Feed appearance (color, texture, etc.) | | |

Aquaculture Animal Characteristics

| | | |
|---|---|---|
| Initial weight | Size variability | Developmental stage |
| Target weight | Stocking density | Body composition (or meat composition) |
| Body condition | Animal or meat color | Survival rate |
| Feedings per day | Feeding activity | Swimming Speed |
| Feed water stability | Desired shelf-life | Specific growth rate |
| Meat yield (e.g., fillet, tail meat, etc.) | Mouth gape | Cost per unit gain |
| FCR | Days to market | Genotype |
| Pigmentation | Feed Consumption | Harvest Biomass |
| Number of days to "X" animal size | $ cost/unit weight gain | % of yield of target product (shrimp tails, fillet, etc.) |
| $ profit/unit production biomass | Return on investment | Cycles per year |
| $ of feed/unit weight of production | $ of feed/$ of biomass | Total harvest biomass |
| % of animals in target size range | Mortality rate | Product shelf life |
| Average animal size | $ of profit/unit of culture area or volume | Average weight gain/week |
| Weight of production/unit of aeration | Species | Days of culture (stocking date) |

Aquaculture Environmental Characteristics

| | | |
|---|---|---|
| System type and size | Ammonia, pH, dissolved oxygen, alkalinity, temp., hardness, etc. | Water flow rate |
| Water exchange rate | Nutrient load | Natural productivity biomass (species specific forage base) |
| Population health | Environmental pathogen load | Temperature, oxygen, etc. variability |

TABLE 1-continued

| System Substrate | Water Filtration Rate | Feed on feeding tray |
| --- | --- | --- |
| Total Filtration Capacity (Mechanical and Chemical) | Photoperiod | Processing form for feed |
| Medicine application | Aeration rate | Nitrogen level |
| Aeration pattern | Feeding tray # and positioning | Feed distribution pattern |
| Secchi disc reading | Immune status | Microbial profile or levels |
| Phosphorus level | | |

Referring now to the components of system 100, supervisor 200 may be any type of system configured to manage the data processing function within system 100 to generate optimization information, as will be further discussed below with reference to FIG. 2. Simulator 300 may be any type of system configured to receive animal information or animal formulation data, apply one or more models to the received information, and generate performance projections such as animal requirements, animal performance projections, environmental performance projections, and/or economic performance projections as will be further discussed below with reference to FIG. 3. Ingredient engine 400 may be any kind of system configured to receive a list of ingredients and generate ingredient profile information for each of the ingredients including nutrient and other information. Formulator 500 may be any type of system configured to receive an animal requirements projection and ingredient profile information and generate animal formulation data, as will be further discussed below with reference to FIG. 4.

Figure 2:
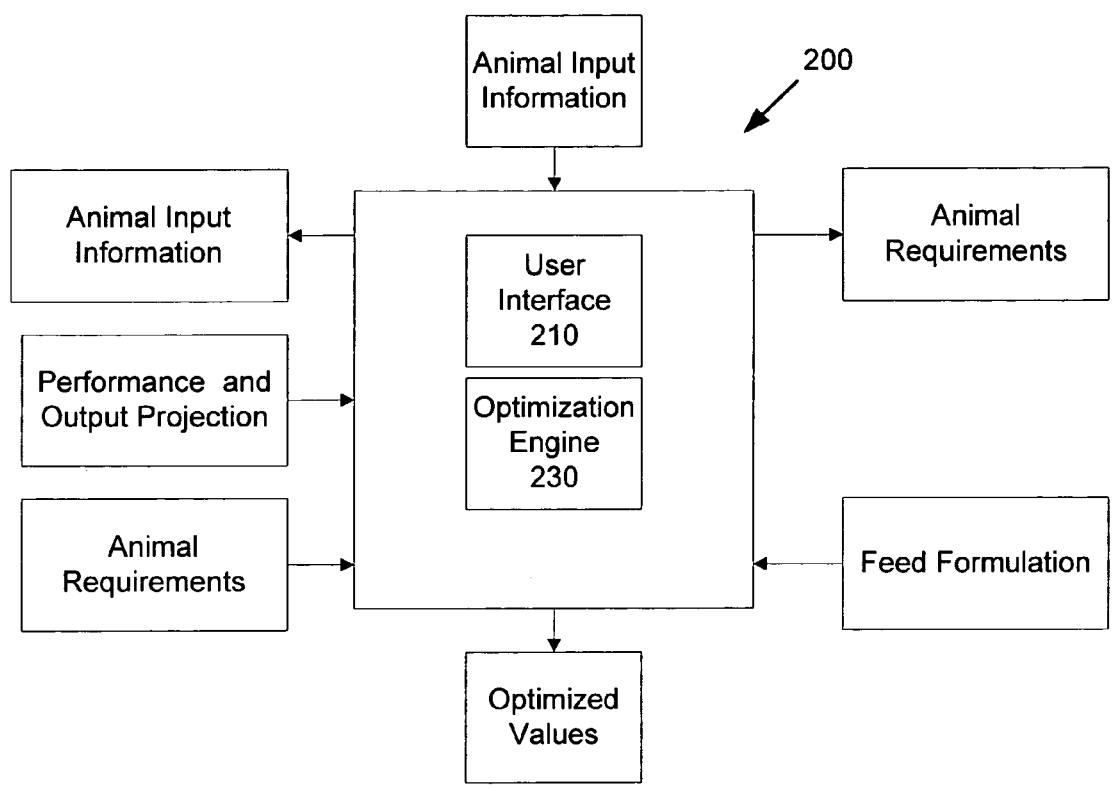
FIG. 2 is a general block diagram illustrating an enterprise supervisor for an animal production optimization system, according to an exemplary embodiment.

Referring now to FIG. 2, a general block diagram illustrating an enterprise supervisor 200 for an animal production optimization system 100 is shown, according to an exemplary embodiment. Enterprise supervisor 200 includes a user interface 210 and an optimization engine 230. Enterprise supervisor 200 may be any type of system configured to receive animal information input through user interface 210, submit the information to simulator 300 to generate at least one animal requirement, submit the at least one animal requirement to formulator 500 to generate least cost animal feed formulation given the animal requirement, submit the optimized formulation to simulator 300 to generate a performance projection and to utilize optimization engine 230 to generate optimized values for one or more variable inputs.

According to an alternative embodiment, optimization or some portion of the optimization may be performed by a different component of system 100. For example, optimization described herein with reference to supervisor 200 may alternatively be performed by simulator 300. Further, optimization of animal feed formulation may be performed by formulator 500.

Enterprise supervisor 200 may include or be linked to one or more databases configured to automatically provide animal information inputs or to provide additional information based upon the animal information inputs. For example, where a user has requested optimization information for a dairy production operation, enterprise supervisor 200 may be configured to automatically retrieve stored information regarding the user's dairy operation that was previously recorded to an internal database and also to download all relevant market prices or other relevant information from an external database or source.

User interface 210 may be any type of interface configured to allow a user to provide input and receive output from system 100. According to an exemplary embodiment, user interface 210 may be implemented as a web based application within a web browsing application. For example, user interface 210 may be implemented as a web page including a plurality of input fields configured to receive animal information input from a user. The input fields may be implemented using a variety of standard input field types, such as drop-down menus, text entry fields, selectable links, etc. User interface 216 may be implemented as a single interface or a plurality of interfaces that are navigable based upon inputs provided by the user. Alternatively, user interface 210 may be implemented using a spreadsheet based interface, a custom graphical user interface, etc.

User interface 210 may be customized based upon the animal information inputs and database information. For example, where a user defines a specific species of animal, enterprise supervisor 200 may be configured to customize user interface 210 such that only input fields that are relevant to that specific species of animal are displayed. Further, enterprise supervisor 200 may be configured to automatically populate some of the input fields with information retrieved from a database. The information may include internal information, such as stored population information for the particular user, or external information, such as current market prices that are relevant for the particular species as described above.

Optimization engine 230 may be a process or system within enterprise supervisor 200 configured to receive data inputs and generate optimization information based on the data inputs and at least one of the optimization criteria. According to an exemplary embodiment, optimization engine 230 may be configured to operate in conjunction with simulator 300 to solve one or more performance projections and calculate sensitivities in the performance projection. Calculating sensitivities in the performance projections may include identifying animal information input or variable inputs that have the greatest effect on overall productivity or other satisfaction of the optimization criteria. Optimization engine 230 may further be configured to provide optimized values for the animal information inputs or variable inputs based on the sensitivity analysis. Optimization may include any improvement to productivity or some other measure according to the optimization criteria. The process and steps in producing the optimized values are further discussed below with reference to FIG. 5.

Optimization criteria may include any criteria, target, or combination of targets or balanced goals that are desirable to the current user. In a preferred embodiment, the optimization criteria is maximizing productivity. Maximizing productivity may include maximizing a single or multiple factors associated with productivity such as total output, output quality, output speed, animal survival rates, etc. Maximizing productivity may further include minimizing negative values associated with the productivity, such as costs, harmful waste, etc. Alternative optimization criteria may include profitability, product quality, product characteristics, feed conversion rate, survival rate, growth rate, biomass/unit space, biomass/feed cost, cost/production day, cycles/year, etc. Alternatively, the optimization criteria may include minimizing according to an optimization criteria. For example, it may be desirable to minimize the nitrogen or phosphorus content of animal excretion.

Where the optimization criteria is used to optimize a target output characteristic, the target value may be a desired value for a characteristic of some output produced by the animal production system. For example, a dairy producer may desire a milk output product having enhanced milk protein. A milk output product having increased protein concentration can increase cheese yield, making the output product more valuable for a cheese producer. To capture this value, the animal producer may, for example, utilize system 100 to obtain a recommendation for modifications to one or more of the variable inputs to generate a diet using amino acid metabolism concepts that will lead to a 0.3% increase in milk protein in animals fed the diet. Another producer may seek milk production that is especially low in fat content to create yogurt. Similar to the milk with increased protein content that diet may be tailored to produce the output having the low fat characteristic. Another desirable characteristic may be a high level of polyunsaturated fat, represented by the amount of linolenic acid C18:3 in milk or animal meat to make the output product healthier for the eventual consumer. Other animal information inputs may also be varied to produce the output having the desired characteristics.

The target output characteristics may also be used to generate recommendations to configure the animal production system to produce output that has reduced or minimized characteristics. The minimized characteristics may be advantageous in reducing harmful or detrimental characteristics of the output. For example, dairy production waste generally has high levels of nitrogen and phosphorus that are regulated by stringent environmental standards. Animal producers often face high costs ensuring compliance with these standards. Accordingly, system 100 may be configured such that the total output product, the amount of waste, or a characteristic of the output product, the nitrogen and phosphorus levels in the waste, is reduced. Producing the optimized waste may include analyzing the nutrients being fed to an animal to avoid overfeeding digestible phosphorus and balancing rumen and cow metabolism to maximize nitrogen retention. Although the analysis may yield clear recommendations, producing optimized waste may require analyzing or presenting opposing recommendations and their projected effects to facilitate the balancing of mutually exclusive advantages between an increase in animal performance and reduced waste management costs.

Managing phosphorus characteristics in output may additionally provide advantages in an aquaculture production system. Phosphorus is an important macromineral for the skeletal development of fish species and key metabolic nutrient for growth and proper metabolism for all aqua species. Insufficient dietary phosphorus in aquafeeds can lead to depression of growth and skeletal formation for aqua species. However, phosphorus is also a key limiting nutrient in freshwater aquaculture systems and excess dietary phosphorus can quickly lead to overproduction of algae causing instability to the health of the system. Excess phosphorus is also undesirable because it is an unnecessary cost.

A formulation system can use available phosphorus nutrient in an aquatic environment in conjunction with a phosphorus nutrient in the animal feed formulation generated by system 100 to meet the needed animal requirement with highly available sources and optimize the excess phosphorus entering the aquatic environment. Empirical data from animal digestibility or environmental samples may be used to increase the precision by which this nutrient is managed in the formulation process.

According to another exemplary embodiment, the targeted characteristic may be the nutrient composition of an aquatic meat product. For example, the targeted characteristic may be the fatty acid profile of the meat product. Aquatic meat products have received considerable recognition for generally containing a healthier profile of fatty acids for human diet than many terrestrial meat sources. The composition of fatty acids in these aquatic meats have largely been based on normal deposition that occurs from consumption of natural foods or artificial feeds, which often contain these fatty acids to meet the animal's requirements. Accordingly, system 100 may be configure to generate and animal feed formulation having an array of fatty acids that, when fed to a target culture species, results in an improved fatty acid profile, i.e., more beneficial to human health. A similar example would involve the use of higher levels of vitamin E and selenium to impart an increased shelf-life to the fillet.

The targeted characteristic may also be non-nutrient related. For example, changing the free amino acid content of meat to change its flavor, limiting the concentrations of or choosing improved bioavailability of nutrients that become toxic when they accumulate in zero water exchange systems, targeting specific levels of beta-carotene, astaxanthin or other pigments that can be used metabolically as an anti-oxidant, Vitamin A precursor, or to impart coloration to the meat or skin, etc.

Target output characteristics may include, but are not limited to, end product composition or characteristics including meat yield as a percentage of body weight, saleable product yield, yield of specific body parts, fatty acid profile, amino acid content, vitamin content, marbling, iodine value, water holding capacity, tenderness, body or product color, pigment level, body or product shelf life, etc. The target output characteristic may also include, but is not limited to, a waste composition or environmental effect, including uneaten food amounts, leaching or loss of nutrients such as nitrogen, ammonia, phosphorus, vitamins, attractants, etc., fecal consistency, fecal/urinary output, including total output, ammonia or nitrogen load in system, phosphorus load in system, organic matter bypass, etc., biological oxygen demand, bypass energy, gaseous emissions, C/N ratio of waste stream etc. Although the above examples are provided, a person of ordinary skill in the art can recognize that the target output characteristic may be any output generated in a production system.

Advantageously, system 100 may optimize across all variable animal information inputs to generate recommendations for producing the output having specified target characteristics at the lowest cost. The recommendation may include a single optimal recommendation or a plurality of recommendations yielding equivalent benefits.

Optimization engine 230 may be configured to implement its own optimization code for applications where feed ingredient information from formulator 500 is combined with other information and/or projections calculated in simulator 300. Optimization problems that coordinate several independent calculation engines, referred to as multidisciplinary optimizations, may be solved using gradient-based methods, or more preferably simplex methods such as Nelder-Mead or Torczon's algorithm. Preferably, optimization engine 230 may be configured to implement a custom combination of a gradient-based method for variables on which the optimization criteria depends smoothly (decision variables fed to simulator 300) and a simplex method for variables on which the objective function has a noisy or discontinuous dependence (diet requirements fed to formulator 500). Alternatively, other optimization methods may be applied, including but not limited to, pseudo-gradient based methods, stochastic methods, etc.

Enterprise supervisor 200 may be further configured to format the optimization results and provide the results as output through user interface 210. The results may be provided as recommended optimized values for the variable inputs. The results may further include recommended values for additional animal information inputs, independent of whether the animal information input was designated as a variable input. The results may further include a projection of the effects of implementation of the optimized values for the variable inputs.

Enterprise supervisor 200 may be configured to implement a Monte Carlo method where a specific set of values is drawn from a set of distributions of model parameters to solve for optimized values for the variable inputs. This process may be repeated many times, creating a distribution of optimized solutions. Based on the type of optimization, enterprise supervisor 200 maybe used to select either the value most likely to provide the optimal solution or the value that gives confidence that is sufficient to meet a target. For example, a simple optimization might be selected which provides a net energy level that maximizes the average daily gain for a particular animal. A Monte Carlo simulation may provide a distribution of requirements including various net energy levels and the producer may select the net energy level that is most likely to maximize the average daily gain.

Enterprise supervisor 200 may further be configured to receive real world empirical feedback based on the application of the optimized values for the variable inputs. The empirical feedback may be used to adjust the variable inputs to further optimize the animal production system. The empirical feedback may further be compared to the performance projections to track the accuracy of the projections. Empirical feedback can be provided using any of a variety of methods such as automated monitoring, manual input of data, etc.

Empirical feedback may be any type of data that is gathered or generated based on observations. The data may be gathered by an automated system or entered manually based on a users observations or testing. The data may be gathered in real-time or on any periodic basis depending on the type of data that is being gathered. This data may also already be represented in the animal information inputs and be updated based on any changing values. The empirical feedback to be monitored will generally include animal information inputs that impact an animal production system product, herd health, etc. on a daily basis. The empirical feedback may include, but is not limited to, environment information, animal comfort information, animal feed information, production system management information, animal information, market conditions or other economic information, etc. For example, in a beef production system, the empirical feedback may include carcass data, linear measurements, ultrasound measurements, daily intakes, etc.

Environment information may include information regarding the animal's environment that may affect animal productivity. For example, temperatures above the thermo-neutral zone may decrease an animal's feed intake. Temperature may also affect a rate of passage, which in turn may have an effect on nutrient digestibility, bypass of protein/amino acids, nutrients in excretion, etc. Temperature may also increase intake of animal feed. For example, wind in cold temperatures will increase maintenance energy for warmth (shivering).

The environmental information may also include non-temperature information. For example, in warm temperatures, wind can assist in cooling requiring less loss of dry matter intake, less energy wasted in cooling attempts (panting). Similarly, increasing relative humidity may decrease cow comfort based on an increased heat load when the temperature is warm/hot.

The empirical feedback may further be dependent on the cow's environment. For example, weather events (sun, snow, rain, mud, etc.) are important for cows housed outside. Weather events can impact the body temperature of the cow and the animal's need for shivering or panting further impacting intakes, digestibility, etc. If cows travel from pasture to parlor, mud or stormy/snowy weather can impact the amount of energy required to get to the parlor and back, raising maintenance requirements.

Other environmental information may be related to the general quality of the animal's environment and the level of stress placed on the animal. For example, animal crowding can have a strong impact on an animal's productivity. In overcrowding conditions, dominant cows will get feed first and remaining cows will get a sorted feed which contains different nutrients than formulated feed. Further, cows also need to spend a certain amount of time lying down in order to maximize production. Yet further, overcrowding may cause cows to lie in alleys resulting in increased potential of stepped on teats and mastitis or stand too long. Other exemplary environmental information may include the amount of light, access to water and feed, proper bedding and stalls to encourage cows to lie down, milking protocol such that cows are not held in a holding pen longer than one hour at a time, etc.

Although the above examples are provide in reference to a cow, it should be understood that the described system and method can be similarly applied to any animal. For example, poultry animals may similarly face stress and/or less than optimal growth based on increased temperature. This additional stress can be reduce by, for example, increasing fan use to cause a direct wind, using intermittent misting, etc.

Other empirical feedback may include analysis of the actual animal feed being consumed by animals. For example, a sample may be taken from the animal feed as it is being fed to animals to analyze the nutrient content and assure that the diet being fed is the diet that was formulated to optimize production. The analysis may include an analysis of ingredients as the arrive at the animal production system. To reduce excessive deviation from a formulated animal feed, more variable ingredients can be used at lower inclusion rates. Similarly, empirical testing may include analysis of the ingredients found naturally at the animal production facility, such as the quality of the water ingested by the animals. Water may deliver some minerals in various amounts or have a specific pH level that should be accounted for in diet formulations Empirical testing may further include monitoring the management practices of the animal production system. Management practice may include feed timing, personnel, production gathering practices, etc. For example, an animal production systems personnel may have an affect on production by having an effect on cow comfort level. The number of people, their experience level, the time it takes to complete tasks, etc. can all impact cow comfort.

Animal management practices also may be monitored. Animal management practices may include any practices that may have an effect on the animals. For example, animal production may be affected be feeding time practices. Feeding timing can impact that quality of feed provided, especially in hot weather. The system may be further configured to monitor the frequency and duration of time during which feed is provided to the animal such that the animal is able to eat.

Animal production gathering practices may also have an effect. Animal production gathering may include any process to obtain the results of the animal production, such as the number of milkings per day, egg gathering frequency, etc. that will influence production potential. More milkings may increase production in well-managed herds. It may also be beneficial to increase milkings in cows just starting their lactations to facilitate production.

Empirical testing may further include monitoring the animals within the animal production system. For example, an animal may be monitored for metabolic indicators. Metabolic indicators may be indicative of metabolic problems such as milk fever, ketosis, imbalances in dietary protein, overheating, etc. Other monitored characteristics may include characteristics that must be tested within a laboratory such as non-esterified fatty acids (NEFA), beta hydroxyl butyrate (BHBA), urine pH, milk urea nitrogen (MUN), blood urea nitrogen (BUN), body temperature, blood AA, manure characteristics, carbon dioxide levels, minerals, fat pad probes for pesticide residue testing, etc. Other characteristics may be monitored through observation, such as animals in heat, limping animals, sick animal, pregnancy, etc. that may not eat and produce as well as normal. Yet other characteristics may be a combination of these categories. Other physiological measurements may include microbial profile or hut histological measurements.

Empirical testing provides the advantage of verifying the accuracy of predictive models generated by simulator 300. Optimization results generated from imperfect models may different from real world results obtained through empirical testing. System 100 may be configured to provide dynamic control based on the empirical testing feedback, adjusting animal information inputs or generate values, such as an animal's feed formulation, to achieve specified targets based on the difference between model results and empirical testing feedback. Further, simulator 300 may be configured to adjust how models are generated based on the data obtained through the empirical testing to increase the accuracy of future models.

Further, enterprise supervisor 200 may be configured to enable dynamic control of models. After setting an initial control action, for example the feed formulation, as will be discussed below with reference to FIG. 5, the animal response may be monitored and compared with the prediction. If the animal response deviates too far from the prediction, a new control action, e.g., feed formulation, may be provided. For example, if the performance begins to exceed prediction, some value may be recovered by switching to a less costly feed formulation, different water flow rate, etc. If performance lags prediction, switching to higher value feed formulation, may help to ensure that the final product targets are met. Although the control action is described above with reference to a feed formulation, the control action may be for any control variable, such as water flow rate, feeding rate, etc. Similarly, the adjustments may be made to that control variable, such as by increasing or decreasing the flow rate, etc.

Figure 3:
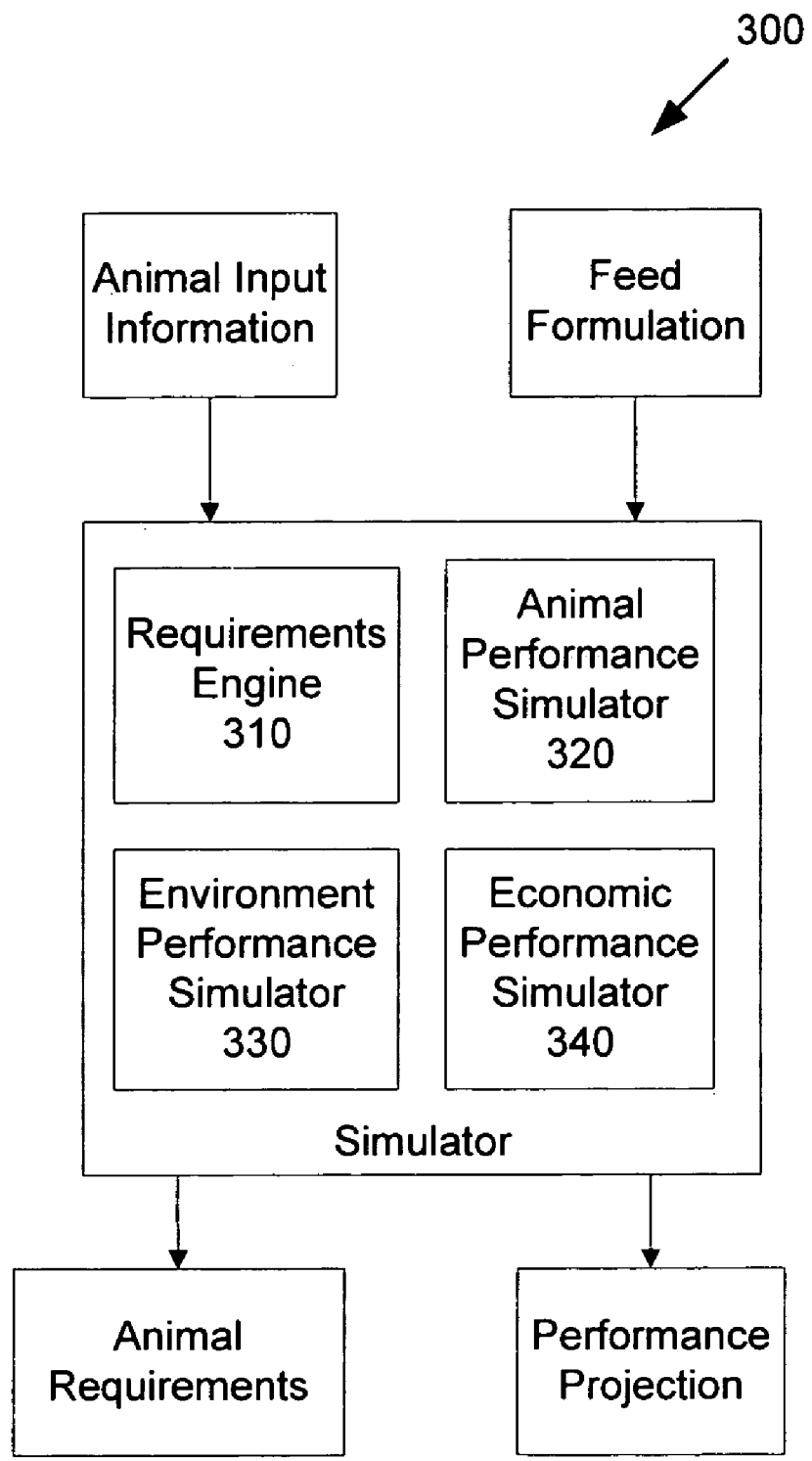
FIG. 3 is a general block diagram illustrating a simulator for an animal production system, according to an exemplary embodiment.

Referring now to FIG. 3, a general block diagram illustrating a simulator 300 is shown according to an exemplary embodiment. Simulator 300 includes a requirements engine 310, an animal performance simulator 320, an environment performance simulator 330, and an economic performance simulator 340. Generally, simulator 300 may be any process or system configured to apply one or more models to input data to produce output data. The output data may include any type of projection or determined value, such as animal requirements and/or performance projections, including animal performance projections, economic performance projections, environmental performance projections, etc.

Specifically, simulator 300 is configured to receive animal information input from enterprise supervisor 200, process the information using requirements engine 310 and an animal requirements model to produce a set of animal requirements. Further, simulator 300 may be configured to receive feed formulation data from enterprise supervisor 200 and process the feed formulation data using any combination of animal performance simulator 320, environment performance simulator 330, and economic performance simulator 340 to produce at least one performance projection.

An animal requirements model, used by simulator 300 to convert input values into one or more outputs, may consist of a system of equations that, when solved, relate inputs like animal size to an animal requirement like protein requirement or a system requirement like space allotment or feed distribution. A specific mathematical form for the model is not required, the most appropriate type of model may be selected for each application. One example is models developed by the National Research Council (NRC), consisting of algebraic equations that provide nutrient requirements based on empirical correlations. Another example is MOLLY, a variable metabolism-based model of lactating cow performance developed by Prof. R. L. Baldwin, University of California-Davis. A model may consist of a set of explicit ordinary differential equations and a set of algebraic equations that depend on the differential variables. A very general model may consist of a fully implicit, coupled set of partial differential, ordinary differential, and algebraic equations, to be solved in a hybrid discrete-continuous simulation.

A model may be configured to be independent of the functionality associated with simulator 300. Independence allows the model and the numerical solution algorithms to be improved independently and by different groups.

Preferably, simulator 300 may be implemented as an equation-based process simulation package in order to solve a wide variety of models within system 100. Equation-based simulators abstract the numerical solution algorithms from the model. This abstraction allows model development independent from numerical algorithms development. The abstraction further allows a single model to be used in a variety of different calculations (steady-state simulation, dynamic simulation, optimization, parameter estimation, etc.). Simulators may be configured to take advantage of the form and structure of the equations for tasks such as the sensitivity calculations. This configuration allows some calculations to be performed more robustly and/or efficiently than is possible when the model is developed as a block of custom computer code. An equation-based process simulation package is software configured to interact directly with the equations that make up a model. Such a simulator typically parses model equations and builds a representation of the system of equations in memory. The simulator uses this representation to efficiently perform the calculations requested, whether steady-state simulations, dynamic simulations, optimization, etc. An equation-based process simulation package also allows incorporation of calculations that are more easily written as combination of procedures and mathematical equations. Examples may include interpolation within a large data table, calling proprietary calculation routines distributed as compiled code for which equations are not available, etc. As newer and better solution algorithms are developed, these algorithms may be incorporated into simulator 300 without requiring any changes to the models simulator 300 is configured to solve.

According to an exemplary embodiment, simulator 300 may be a process simulator. Process simulators generally include a variety of solution algorithms such as reverse mode automatic differentiation, the staggered corrector method for variable sensitivities, automatic model index reduction, robust Newton iteration for solving nonlinear systems from poor initial values, error-free scaling of variable systems, and the interval arithmetic method for locating state events. Process simulators utilize sparse linear algebra routines for direct solution of linear systems. The sparse linear algebra routines can efficiently solve very large systems (hundreds of thousands of equations) without iteration. Process simulators further provide a particularly strong set of optimization capabilities, including non-convex mixed integer non-linear problems (MINLPs) and global variable optimization. These capabilities allow simulator 300 to solve optimization problems using the model directly. In particular, the staggered corrector algorithm is a particularly efficient method for the sensitivities calculation, which is often the bottleneck in the overall optimization calculation.

Variable inputs for optimization to be solved by simulator 300 may include both fixed and time-varying parameters. Time varying parameters are typically represented as profiles given by a set of values at particular times using a specific interpolation method, such as piecewise constant, piecewise linear, Bezier spline, etc.

Simulator 300 and the associated models may be configured and structured to facilitate periodic updating. According to an exemplary embodiment, simulator 300 and the associated models may be implemented as a dynamic link library (DLL). Advantageously, a DLL may be easily exported but not viewed or modified in any structural way.

Requirements engine 310 may be any system or process configured to receive animal information input and generate animal requirements by applying one or more requirements models to the set of animal information input. A requirements model may be any projection of potential outputs based upon any of a variety of set of inputs. The model may be as simple as a correlation relating milk production to net energy in an animal feed or as complex as a variable model computing the nutrient requirement to maximize the productivity of a shrimp aquaculture pond ecosystem. Requirements engine 310 may be configured to select from a plurality of models based on the animal information inputs. For example, requirements engine 310 may include models for swine requirements, dairy requirements, companion animal requirements, equine requirements, beef requirements, general requirements, poultry requirements, aquaculture animal requirements, etc. Further, each model may be associated with a plurality of models based on an additional categorization, such as developmental stage, stress level, etc.

Animal requirements generated by requirements engine 310 may include a listing of nutrient requirements for a specific animal or group of animals. Animal requirements may be a description of the overall diet to be fed to the animal or group of animals. Animal requirements further may be defined in terms of a set of nutritional parameters ("nutrients"). Nutrients and/or nutritional parameters may include those terms commonly referred to as nutrients as well as groups of ingredients, microbial measurements, indices of health, relationships between multiple ingredients, etc. Depending on the degree of sophistication of system 100, the animal requirements may include a relatively small set of nutrients or a large set of nutrients. Further, the set of animal requirements may include constraints or limits on the amount of any particular nutrient, combination of nutrients, and/or specific ingredients. Advantageously, constraints or limits are useful where, for example, it has been established at higher levels of certain nutrients or combination of nutrients could pose a risk to the health of an animal being fed. Further, constraints may be imposed based on additional criteria such as moisture content, palatability, etc. The constraints may be minimums or maximums and may be placed on the animal requirement as a whole, any single ingredient, or any combination ingredients. Although described in the context of nutrients, animal requirements may include any requirements associated with an animal, such as space requirements, heating requirements, etc.

Additionally, animal requirements may be generated that define ranges of acceptable nutrient levels. Advantageously, utilizing nutrient ranges allows greater flexibility during animal feed formulation, as will be described further below with reference to FIG. 3.

Requirements engine 310 may be further configured to account for varying digestibility of nutrients. For example, digestibility of some nutrients depends on the amount ingested. For example, wherein an animal ingests a quantity of phosphorous in a diet, the percentage that is utilized by the animal may decrease in relation to the quantity ingested. An animal's digestive tract may only be able utilize a certain amount of phosphorous and the remainder will be passed through the animal. Accordingly, phosphorous utilization may have an inverse relationship with the amount of phosphorous in an animal feed after a certain level is reached. Digestibility may further depend on the presence or absence of other nutrients, microbes and/or enzymes, processing effects (e.g. gelatinization, coating for delayed absorption, etc.), animal production or life stage, previous nutrition level, etc. Simulator 300 may be configured to account for these effects. For example, simulator 300 may be configured to adjust a requirement for a particular nutrient based on another particular nutrient additive.

Requirements engine 310 may also be configured to account for varying digestion by an animal. Animal information inputs may include information indicating the health of an animal, stress level of an animal, reproductive state of an animal, methods of feeding the animal, etc. as it affects ingestion and digestion by an animal. Shifts based on immune status may cause an increased maintenance cost to engage protective systems, while reducing voluntary nutrient intake. For example, the stress level of an animal may decrease the overall feed intake by the animal, while gut health may increase or decrease a rate of passage. According to another example, changes in a microbial profile for an animal may indicate a shift in digestion of nutrients from enzymatic digestion to bacterial fermentation.

Table 2 below includes an exemplary listing of nutrients that may be included in the animal requirements. According to an exemplary embodiment, within the animal requirements, each listed nutrient may be associated with a value, percentage, range, or other measure of amount. The listing of nutrients may be customized to include more, fewer, or different nutrients based on any of a variety of factors, such as animal type, animal health, nutrient availability, etc.

TABLE 2

Nutrients Suitable for Generating Animal Requirements

| | | |
|---|---|---|
| ADF | Animal Fat | Ascorbic Acid |
| Arginine (Total and/or Digestible) | Ash | Biotin |
| Calcium | Calcium/Phos ratio | Chloride |
| Choline | Chromium | Cobalt |

TABLE 2-continued

Nutrients Suitable for Generating Animal Requirements

| | | |
|---|---|---|
| Copper | Cystine (Total and/or Digestible) | Dry Matter |
| Fat | Fiber | Folic Acid |
| Hemicellulose | Iodine | Iron |
| Isoleucine (Total and/or Digestible) | Lactose | Lasalocid |
| Leucine (Total and/or Digestible) | Lysine (Total and/or Digestible) | Magnesium |
| Manganese | Margin | Methionine (Total and/or Digestible) |
| Moisture | Monensin | NDF |
| NEg (Net Energy for Gain) | NEl (Net Energy Lactation) | NEm (Net Energy for Maintenance) |
| NFC (Non-Fiber Carbohydrate) | Niacin | Phenylalanine (Total and/or Digestible) |
| Phosphorus | Phosphate | Potassium |
| Protein | Pyridoxine | Rh Index (Rumen Health Index) |
| Riboflavin | Rough NDF | Rum Solsug (Rumen Soluble Sugars) |
| Rumres NFC (Ruminant Residual Non-Fiber Carbohydrate) | RUP (Rumen Undegradable Protein) | Salt |
| Selenium | Simple Sugar | Sodium |
| Sol RDP (Soluble Rumen Degradable Protein) | Sulfur | ME (Metabolizable Energy) |
| Thiamine | Threonine (Total and/or Digestible) | Total RDP |
| Tryptophan (Total and/or Digestible) | Valine (Total and/or Digestible) | Vitamin A |
| Vitamin B12 | Vitamin B6 | Vitamin D |
| Vitamin E | Vitamin K | Zinc |
| Gut Health Index | Fatty Acids (EPA, DHA, Linolenic, etc.) | Cholesterol |
| Phospholipids | UFC | |

Requirements engine 310 may be configured to generate the animal requirements based on one or more requirement criteria. Requirement criteria can be used to define a goal for which the requirement should be generated. For example, exemplary requirement criteria can include economic constraints, such as maximizing production, slowing growth to hit the market, or producing an animal at the lowest input cost. The animal requirements may be used to generate an animal feed formulation for an animal. Accordingly, the animal requirements may be used as animal feed formulation inputs.

The requirements engine 310 may further be configured to generate the animal requirements based on one or more dynamic nutrient utilization models. Dynamic nutrient utilization may include a model of the amount of nutrients ingested by an animal feed that are utilized by an animal based on information received in the animal information inputs, such as animal health, feeding method, feed form (mash, pellets, extruded, particle size, etc.), water stability of feed, uneaten food, water temperature and its impact on enzyme levels, etc. Nutrient utilization may further depend on the presence or absence of other nutrient additives, microbes and/or enzymes, processing effects (e.g. gelatinization, coating for delayed absorption, etc.), animal production or life stage, previous nutrition level, etc.

Simulator 300 may be configured to account for these effects. For example, simulator 300 may be configured to adjust the level of a particular nutrient, defined in an animal feed formulation input, from the level determined based on the animal requirement to a different level based on the presence or absence of another particular nutrient. Using the above example for phosphorous, the amount of phosphorous that is utilized by an animal may also be affected by other nutrients in the animal's diet. For example, the presence of a particular microbe in an animal's digestive track, whether naturally present or added as a nutrient, may actually increase the phosphorous utilization beyond the levels that would normally occur and reduce the amount that enters an animal's waste stream.

Accordingly, an animal feed formulation input may be modified based on the nutrient utilization model. However, this change in the animal feed formulation may have an effect on the animal feed formulation, including the animal feed formulation that was just modified. Accordingly, compensating for a nutrient utilization model may require an iterative calculation, constantly updating values, to arrival at a final value that is within a predefined tolerance.

Requirements engine 310 may also be configured to account for variations in digestion and utilization of nutrients by an animal. Animal information inputs may include information indicating the health of an animal, stress level of an animal, reproductive state of an animal, methods of feeding the animal, etc. as it affects ingestion and digestion by an animal. For example, the stress level of an animal may decrease the overall feed intake by the animal, while gut health may increase or decrease a rate of passage. Alternatively, a stress level may alter the actual metabolism for an animal. For example, an animal's metabolism may be altered by a stress-induced release of cortisone. Other exemplary metabolic modifiers may include immune system cascades of prostaglandins and other pro-inflammatory cytokines, leukocytes, antibodies, and other immune cells and substances, growth promoting implants, and adrenergic feed additives. These reactions shift site and extent of digestion, change nutrient intake, and force digested nutrients towards a more catabolic state.

Animal performance simulator 320 may be a process or system including a plurality of models similar to the models described above with reference to requirements engine 310. The models utilized in animal performance simulator 320 receive an animal feed formulation from formulator 300 through enterprise supervisor 200 and the animal information inputs and apply the models to the feed formulation to produce one or more animal performance projections. The animal performance projection may be any predictor of animal productivity that will be produced given the animal feed formulation input and other input variables.

Environment performance simulator 330 may be a process or system including a plurality of models similar to the models described above with reference to requirements engine 310. The models utilized in environment performance simulator 330 receive animal feed formulation from formulator 300 through enterprise supervisor 200 and apply the models to the feed formulation and animal information inputs to produce a performance projection based on environmental factors. The environmental performance projection may be any prediction of performance that will be produced given the animal feed formulation input, animal information inputs, and environmental factors.

Economic performance simulator 340 may be a process or system including a plurality of models similar to the models described above with reference to requirements engine 310. The models utilized in economic performance simulator 340 receive animal feed formulation from formulator 300 through enterprise supervisor 200 and apply the models to the feed formulation and animal information inputs to produce a performance projection based on economic factors. The economic performance projection may be any prediction of performance that will be produced given the animal feed formulation input, animal information inputs, and the economic factors.

The performance projections may include a wide variety of information related to outputs produced based on the provided set inputs. For example, performance projections may include information related to the performance of a specific animal such as the output produced by an animal. The output may include, for example, the nutrient content of eggs produced by the animal, qualities associated with meat produced by the animal, the contents of waste produced by the animal, the effect of the animal on an environment, etc.

According to exemplary embodiment, simulators 320, 330, and 340 may be run in parallel or in series to produce multiple performance projections. The multiple animal performance projections may remain separated or be combined into a single comprehensive performance projection. Alternatively, performance projections may be generated based on a single simulator or a combination of less than all of the simulators.

Requirements engine 310 may further include additional simulators as needed to generate performance projections that are customized to satisfy a specific user criteria. For example, requirements engine 310 may include a bulk composition simulator, egg composition simulator, meat fat composition, waste output simulator, maintenance energy calculator, etc.

Figure 4:
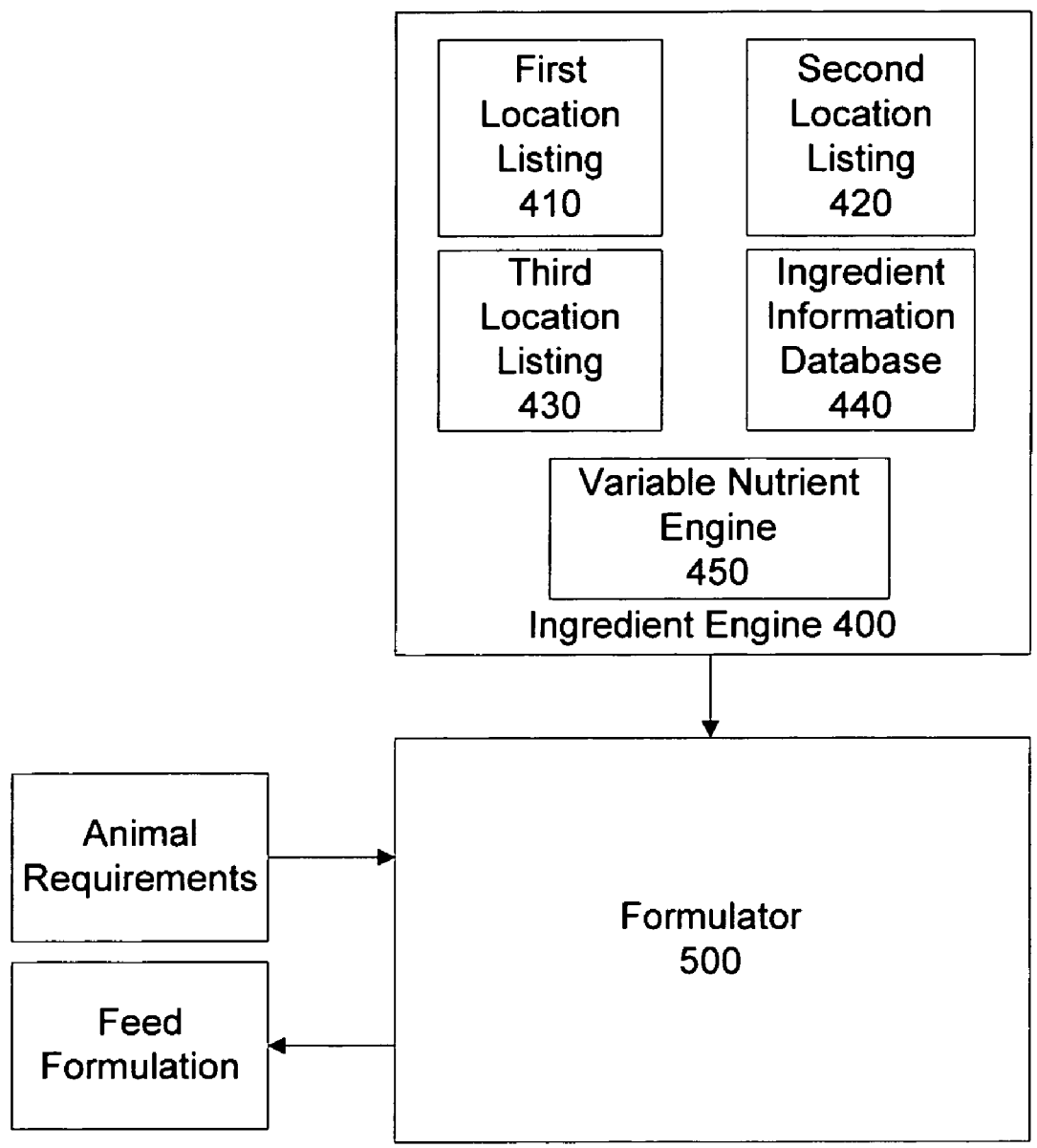
FIG. 4 is a general block diagram illustrating an ingredients engine and a formulator for an animal production system, according to an exemplary embodiment.

Referring now to FIG. 4, a general block diagram illustrating an ingredients engine 400 and a formulator 500 is shown, according to an exemplary embodiment. Ingredients engine 400 is configured to exchange information with formulator 500. Ingredients engine 400 and formulator 500 are generally configured to generate an animal feed formulation based on available ingredients and received animal requirements.

Ingredients engine 400 includes one or more listings of available ingredients at one or more locations. The listing further includes additional information associated with the ingredients, such as the location of the ingredient, nutrients associated with the ingredient, costs associated with the ingredient, etc.

Ingredients engine 400 may include a first location listing 410, a second ingredient location listing 420, and a third ingredient location listing 430. First ingredient listing 410 may include a listing of ingredients available at a first location, such as ingredients at a user's farm. The second ingredient listing 420 may include a listing of ingredients that are available for purchase from an ingredient producer. Third ingredient listing 430 may include a listing of ingredients that are found in a target animal's environment such as forage in a pasture, plankton (zooplankton, phytoplankton, etc.), or small fish in an aquaculture pond, etc. The listing of ingredients may further include environmental nutrient inputs. Environmental nutrient inputs may be any nutrient or nutrients that are received and/or utilized by an animal that is not fed to the animal.

Referring now to third ingredient listing 430, an example of a listing of ingredients that are found in a target animal's environment may include a listing of the mineral content of water. An animal's total water consumption can be estimated based on known consumption ratios, such as a ratio of water to dry feed matter consumed. Consumption of an ingredient or nutrient may include actual consumption as well as receipt by an animal through absorption, generation through body processes, etc. This ratio may be either assigned an average value or, more preferably, calculated from known feed and animal properties. The mineral content of the water provided by producer may be measured on-site. This water, with measured mineral content and calculated intake level, may be incorporated in third ingredient listing 430. Although mineral content is provided as an example, it should be understood that the listing of ingredient may include any nutrient level or characteristic of the water such as the water pH level.

Alternatively, third ingredient listing 430 may include an aquatic ecosystem total nutrient content. The ecosystem contribution to total nutrition may be included in several ways. For example, a sample may be drawn and analyzed for total nutrient content and included as third listing 430. Preferably, the models solved in simulator 300 may be expanded to include not only that species being produced but other species that live in the ecosystem as well. The model may include one or more of the following effects: other species competition for feed, produced species consumption of other species in ecosystem, and other species growth over time in response to nutrient or toxin excretion, temperature, sunlight, etc. The models may further account for consumption/utilization of the environmental nutrient inputs based on the life stage of the animal, knowledge of growing conditions, analysis of ingredients, etc.

Further, third ingredient listing 430 may be representative of a closed nutrient system, wherein outputs generated from an animal feed being fed to an animal are treated as inputs to generate third ingredient listing 430. For example, an animal may be initially fed a diet composed of nutrients from first ingredient listing 410 and/or second ingredient listing 420. The animal's utilization of the nutrient composition may be determined within simulator 300, described in further detail below, and provided to formulator 500 for optimization versus established animal requirements. Simulator 300 may further be configured to generate a projection of the quantity and quality of nutrients that are not utilized by the animal and/or nutrients in the animal's waste that are provided to the animal's environment.

The output of un-utilized nutrient or waste stream nutrients may then be used for projecting changes to the animal's environment and the composition of third ingredient listing 430. For example, where the animal is an aquatic animal, such as a shellfish, the output from the shellfish may be used in calculating projected changes in the algae standing stock. This modified algae standing stock is then considered an ingredient in third ingredient listing 430 to the extent that the animals consume the algae standing stock as part of its diet. The additional ingredient may reduce or otherwise modify the animal's calculated requirements. It can be appreciated how the above described interaction may be used to create a number of cyclical feedback loops to optimize the animal production. Further, an optimized animal feed may be optimized based on the requirements of the entire ecosystem biomass in addition to the animal.

According to yet another exemplary embodiment, the performance projections generated by simulator 300 may be used to estimate the biomass and nutrient content of a first species, that is a food source for a second species. The first species may be algal, bacterial, invertebrate, or vertebrate. Accordingly, the output of simulator 300 may be used to define the ingredients in third ingredient listing 430, including bioavailability and total nutrient provision. For example, wherein the first species is brine shrimp and the second species is an aquarium salt water fish, simulator 300 may be utilized to generate a recommendation for optimizing the growth rate and/or nutrient content of the brine shrimp. The brine shrimp population may also be calculated in view of feeding projections for the salt water aquarium fish. These brine shrimp may then be components within third ingredient listing 430 and may be used as components in formulating an optimized animal feed for the salt water aquarium fish. Specifically, the ingredients in third ingredient listing 430 may be provided to variable nutrient engine 450, discussed below, and formulator 500. Further, the performance projections associated with the first animal may be used to project future components within third ingredient listing 430 and their characteristics.

As shown in the above example, simulator 300, in combination with third ingredient listing 430, may be used to model an entire interaction between an animal, the organisms in its environment, and the environment itself. The interaction may be used to satisfy current animal requirements and to generate projections for the animal, other organisms, and the environment.

For example, the environment of third ingredient listing 430 may include ingredients and associated nutrients within a wheat grass pasture. The pasture may be fertilized with nitrogen, potassium, and phosphorus. The fertilizer may be naturally occurring, such as from cow manure or poultry litter, or man-made, such as a chemical fertilizer.

The pasture may be managed by an animal producer such that the wheat grass does not get more mature than an early boot stage, an optimum maturity for nutrient quality. Upon maturity, the pasture may be grazed by 400 pound stocker calves for about two months. It is recognized that the animal, during grazing will generally fertilize the wheat grass naturally. As the calves graze they will continuously gain weight, which is made up primarily of minerals, water, and protein. Accordingly, the nitrogen, potassium, and phosphorus that is used to fertilize the wheat grass become a nutritional component of the calves.

After the cattle are removed from the pasture, the animal producer may choose to allow the wheat grass to grow to maturity for harvesting. The harvested wheat grass may be turned directly into another food source, such as flour for bread, or it may be used as bedding in a feedlot. Wheat grass used for bedding may eventually be collected from the feedlot, along with manure from the cattle in the feedlot and put back in the pasture. The nutrients in the straw and manure may be disked down into the field and are taken up by the roots of the next crop of wheat grass.

Accordingly, system 100, using simulator 300, ray be configured to iteratively analyze variable inputs that effect not only the animals, but also the environment of the animal, which may in turn affect the animals. Each projection by simulator 300 may be iteratively performed to determine the effects on related inputs based on the current projections.

Third ingredient listing 430 may further include performance projections generated by simulator 300. For example, the nutrient content of milk may be modeled for the particular animals for an individual producer. This milk nutrient content model may be used as a third ingredient listing 430 for consumption by a nursing animal.

Each listing of ingredients may further include additional information associated with the ingredients. For example, a listing of ingredients may include a listing of costs associated with that ingredient. Alternatively, an ingredient at the first location may include a costs associated with producing the ingredient, storing the ingredient, dispensing the ingredient, etc., while an ingredient at the second location may include a cost associated with purchasing the ingredient, and an ingredient at the third location may include a cost associated with increasing the biomass, changing the nutrient profile, altering nutrient availability, etc. The additional information may include any type of information that may be relevant to later processing steps.

Table 3 below includes an exemplary list of ingredients which may be used in generating the animal feed formulation. The listing of ingredients may include more, fewer, or different ingredients depending on a variety of factors, such as ingredient availability, entry price, animal type, etc.

TABLE 3

Exemplary Ingredients Suitable for Use in Formulating Custom Feed Mixes

| | | |
|---|---|---|
| Acidulated Soap Stocks | Active Dry Yeast | Alfalfa Meal |
| Alfalfa-Dehydrated | Alimet | Alka Culture |
| Alkaten | Almond Hulls | Ammonium Chloride |
| Ammonium Lignin | Ammonium Polyphosphate | Ammonium Sulfate |
| Amprol | Amprol Ethopaba | Anhydrous Ammonia |
| Appetein | Apramycin | Arsanilic Acid |
| Ascorbic Acid | Aspen Bedding | |
| Avizyme | Bacitracin Zinc | Bakery Product |
| Barley | Barley-Crimped | Barley-Ground |
| Barley-Hulless | Barley-Hulls | Barley-Midds |
| Barley-Needles | Barley-Rolled | |
| Barley-Whole | Barley-With Enzyme | Baymag |
| | | Beet |
| Beet Pulp | Biotin | Biscuit By Product |
| Black Beans | Blood-Flash Dry | |
| Bone Meal | Brewers Rice | Brix Cane |
| Buckwheat | | Cage Calcium |
| Calcium Cake | Calcium Chloride | Calcium Formate |
| Calcium Iodate | Calcium Sulfate | Calcium Prop |
| | Canadian Peas | Cane-Whey |
| Canola Cake | Canola Fines | Canola Meal |
| Canola Oil | Canola Oil Blender | Canola Oil Mix |
| Canola Screenings | Canola-Whole | Carbadox |
| Carob Germ | Carob Meal | Cashew Nut Byproduct |
| Catfish Offal Meal | Choline Chloride | Chromium Tripicolinate |
| Citrus Pulp | Clopidol | Cobalt |
| Cobalt Carbonate | Cobalt Sulfate | Cocoa Cake |
| Cocoa Hulls | Copper Oxide | Copper Sulfate |
| Corn Chips | Corn Chops | Corn Coarse Cracked |
| Corn-Coarse Ground | Corn Cob-Ground | Corn Distillers |
| Corn Flint | Corn Flour | Corn Germ Bran |
| Corn Germ Meal | Corn Gluten | Corn-High Oil |
| Corn Kiblets | Corn Meal Dehulled | Corn Oil |

TABLE 3-continued

Exemplary Ingredients Suitable for Use in Formulating Custom Feed Mixes

| | | |
|---|---|---|
| Corn Residue | Corn Starch | Corn/Sugar Blend |
| Corn-Cracked | Corn-Crimped | Corn-Ground Fine |
| Corn-Ground Roasted | Corn-Steam Flaked | Corn-Steamed |
| Corn-Whole | Cottonseed Culled | Cottonseed Hull |
| Cottonseed Meal | Cottonseed Oil | Cottonseed Whole |
| Coumaphos | Culled Beans | Danish Fishmeal |
| Decoquinate | Dextrose | Diamond V Yeast |
| Disodium Phosphate | Distillers Grains | Dried Apple Pomace |
| Dried Brewers Yeast | Dried Distillers Milo | Dried Porcine |
| Dried Whole Milk Powder | Duralass | Enzyme Booster |
| Epsom Salts | | Extruded Grain |
| Extruded Soy Flour | Fat | Feather Meal |
| Feeding Oatmeal | Fenbendazole | Fermacto |
| Ferric Chloride | Ferrous Carbonate | Ferrous Carbonate |
| Ferrous Sulfate | Fine Job's Tear Bran | Fish Meal |
| Fish | Flavoring | Folic Acid |
| | Fresh Arome | Fried Wheat Noodles |
| Gold Dye | Gold Flavor | Grain Dust |
| Grain Screening | Granite Grit | Grape Pomace |
| Green Dye | Green Flavor | Guar Gum |
| Hard Shell | Hemicellulose Extract | |
| Herring Meal | Hominy | Hygromycin |
| Indian Soybean Meal | Iron Oxide-Red | Iron-Oxide Yellow |
| Job's Tear Broken Seeds | | Kelp Meal |
| Kem Wet | Lactose | Larvadex |
| Lasalocid | Levams Hcl | Limestone |
| Linco | Lincomix | Lincomycin |
| Linseed Meal | Liquid Fish Solubles | Lupins |
| Lysine | Magnesium | Magnesium Sulfate |
| Malt Plant By-Products | Manganous Ox | Maple Flavor |
| Masonex | Meat And Bone Meal | Meat Meal |
| Mepron | Methionine | Millet Screenings |
| Millet White | Millet-Ground | Milo Binder |
| Milo-Coarse Ground | Milo-Cracked | Milo-Whole |
| Mineral Flavor | Mineral Oil | Mixed Blood Meal |
| Molasses | Molasses Blend | Molasses Dried |
| Molasses Standard Beet | Molasses Standard Cane | Molasses-Pellet |
| Mold | Monensin | Monoamunum Phos |
| Monosodium Glutamate | Monosodium Phosphate | Mung Bean Hulls |
| Mustard Meal High Fat | Mustard Oil | Mustard Shorts |
| Narasin | Natuphos | Niacin |
| Nicarbazin | Nitarsone | Oat Cullets |
| Oat Flour | Oat Groats | Oat Hulls |
| Oat Mill Byproducts | Oat Screenings | Oat Whole Cereal |
| Oatmill Feed | Oats Flaked | Oats-Ground |
| Oats-Hulless | Oats-Premium | Oats-Rolled |
| Oats-Whole | Oyster Shell | Paddy Rice |
| Palm Kernel | Papain | Papain Enzyme |
| Paprika Spent Meal | Parboiled Broken Rice | Pea By-Product |
| Pea Flour | Peanut Meal | Peanut Skins |
| Pelcote Dusting | Phosphate | Phosphoric Acid |
| Phosphorus | Phosphorus Defluorinated | Pig Nectar |
| | Poloxalene | Popcorn |
| Popcorn Screenings | Porcine Plasma; Dried | Pork Bloodmeal |
| Porzyme | Posistac | Potassium Bicarbonate |
| Potassium Carbonate | Potassium Magnesium Sulfate | Potassium Sulfate |
| Potato Chips | Poultry Blood/Feather Meal | Poultry Blood Meal |
| Poultry Byproduct | Predispersed Clay | Probios |
| Procain Penicillen | Propionic Acid | Propylene Glycol |
| Pyran Tart | Pyridoxine | Quest Anise |
| Rabon | Rapeseed Meal | Red Flavor |
| Red Millet | Riboflavin | Rice Bran |
| Rice By-Products Fractions | Rice Dust | Rice Ground |
| Rice Hulls | Rice Mill By-Product | Rice Rejects Ground |
| Roxarsone | Rumen Paunch | Rumensin |
| Rye | Rye Distillers | Rye With Enzymes |
| Safflower Meal | Safflower Oil | Safflower Seed |
| Sago Meal | Salinomycin | Salt |
| Scallop Meal | Seaweed Meal | Selenium |
| Shell Aid | Shrimp Byproduct | Silkworms |
| Sipernate | Sodium Acetate | Sodium Benzoate |
| Sodium Bicarbonate | Sodium Molybdate | Sodium Sesquicarbonate |
| Sodium Sulfate | Solulac | |
| Soy Flour | Soy Pass | Soy Protein Concentrate |
| Soybean Cake | Soybean Curd By-Product | Soybean Dehulled Milk By-Product |

TABLE 3-continued

Exemplary Ingredients Suitable for Use in Formulating Custom Feed Mixes

| | | |
|---|---|---|
| Soybean Hulls | Soybean Mill Run | Soybean Oil |
| Soybean Residue | Soybeans Extruded | Soybeans-Roasted |
| Soycorn Extruded | Spray Dried Egg | Standard Micro Premix |
| Starch Molasses | Steam Flaked Corn | Steam Flaked Wheat |
| Sugar (Cane) | Sulfamex-Ormeto | Sulfur |
| Sunflower Meal | Sunflower Seed | Tallow Fancy |
| Tallow-Die | Tallow-Mixer | Tapioca Meal |
| Tapioca Promeance | Taurine | Terramycin |
| Thiabenzol | Thiamine Mono | Threonine |
| Tiamulin | Tilmicosin | Tomato Pomace |
| Trace Min | Tricalcium Phosphate | Triticale |
| Tryptophan | Tryptosine | Tuna Offal Meal |
| Tylan | Tylosin | Urea |
| Vegetable Oil Blend | Virginiamycin | Vitamin A |
| Vitamin B Complex | Vitamin B12 | Vitamin D3 |
| Vitamin E | Walnut Meal | Wheat Bran |
| Wheat Coarse Ground | Wheat Germ Meal | Wheat Gluten |
| Wheat Meal Shredded | Wheat Millrun | Wheat Mix |
| Wheat Noodles Low Fat | Wheat Red Dog | Wheat Starch |
| Wheat Straw | Wheat With Enzyme | Wheat-Ground |
| Wheat-Rolled | Wheat-Whole | Whey Dried |
| Whey Permeate | Whey Protein Concentrate | Whey-Product Dried |
| Yeast Brewer Dried | Yeast Sugar Cane | Zinc |
| Zinc Oxide | Zoalene | |

Ingredient engine 400 may further include an ingredient information database 440. Ingredient information database 440 may include any kind of information related to ingredients to be used in generating the feed formulation, such as nutrient information, cost information, user information, etc. The information stored in database 440 may include any of a variety of types of information such as generic information, information specifically related to the user, real-time information, historic information, geographically based information, etc. Ingredient information database 440 may be utilized by ingredient engine 400 to supply information necessary for generating an optimized feed formulation in conjunction with information supplied by the user.

Ingredient information database 440 may further be configured to access external databases to acquire additional relevant information, such as feed market information. Feed market information may similarly include current prices for ingredient, historical prices for output, ingredient producer information, nutrient content of ingredient information, market timing information, geographic market information, delivery cost information, etc. Ingredient information database 440 may further be associated with a Monte Carlo type simulator configured to provide historical distributions of ingredient pricing and other information that can be used as inputs to other components of system 100.

Ingredient engine 400 may further include a variable nutrient engine 450 configured to provide tracking and projection functions for factors that may affect the nutrient content of an ingredient. For example, variable nutrient engine 450 may be configured to project the nutrient content for ingredients over time. The nutrient content for some ingredients may change over time based on method of storage, method of transportation, natural leaching, processing methods, etc. Further, variable nutrient engine 450 may be configured to track variability in nutrient content for the ingredients received from specific ingredient producers to project a probable nutrient content for the ingredients received from those specific ingredient producers.

Variable nutrient engine 450 maybe further configured to account for variability in nutrient content of ingredients. The estimation of variability of an ingredient may be calculated based on information related to the particular ingredient, the supplier of the ingredient, testing of samples of ingredient, etc. According to exemplary embodiment, recorded and/or estimated variability and covariance may be used to create distributions that are sampled in a Monte Carlo approach. In this approach, the actual nutrient content of ingredients in an optimized feed formulation are sampled repeatedly from these distributions, producing a distribution of nutrient contents. Nutrient requirements may then be revised for any nutrients for which the nutrient content is not sufficient; The process may be repeated until the desired confidence is achieved for all nutrients. The actual nutrient content for the ingredients may be used to generate an animal feed formulation for an animal. Accordingly, the nutrient content for the ingredients may also be used as animal feed formulation inputs.

Referring now to formulator 500, formulator 500 is configured to receive animal requirements from simulator 300 through enterprise supervisor 200 and nutrient information from ingredients engine 400 based on available ingredients and generate an animal feed formulation. Formulator 500 calculates a least-cost feed formulation that meets the set of nutrient levels defined in the animal requirements.

The least-cost animal feed formulation may be generated using linear programming optimization, as is well-known in the industry. The least-cost formulation is generally configured to utilize a users available ingredients in combination with purchased ingredients to create an optimized feed formulation. More specifically, the linear programming will incorporate nutrient sources provided by a user such as grains, forages, silages, fats, oils, micronutrients, or protein supplements, as ingredients with a fixed contribution to the total feed formulation. These contributions are then subtracted from the optimal formulation; the difference between the overall recipe and these user-supplied ingredients constitute the ingredient combinations that would be produced and sold to the customer.

Alternatively, the formulation process may be performed as a Monte Carlo simulation with variability in ingredient pricing included as either historical or projected ranges to created distribution which are subsequently optimized as described above.

Figure 5:
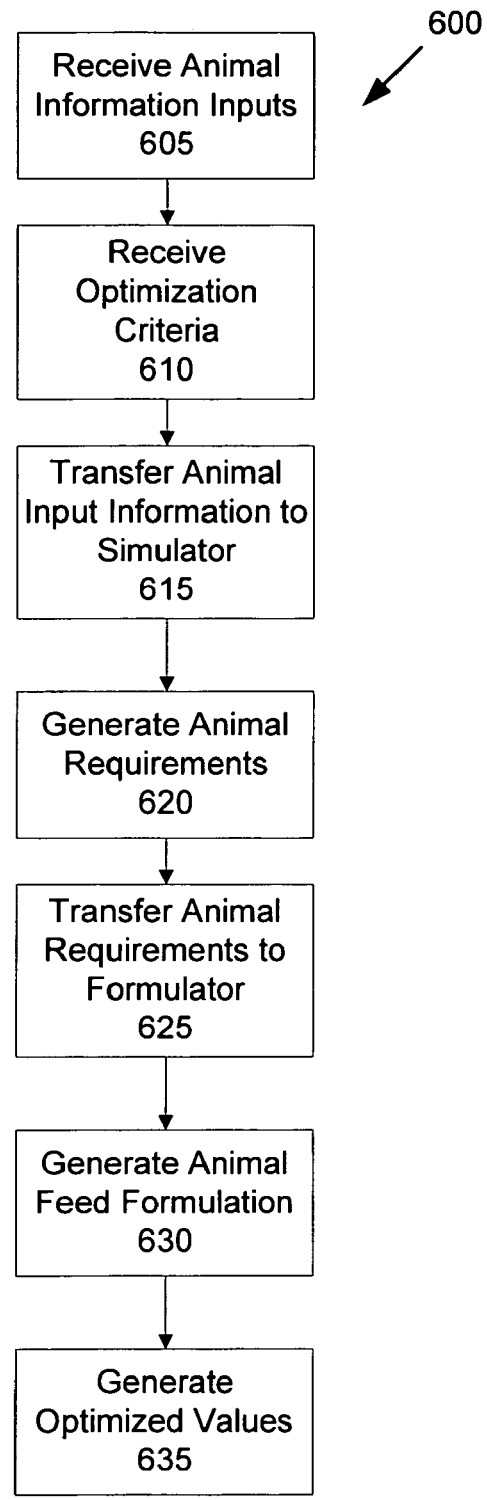
FIG. 5 is a flowchart illustrating a method for animal production optimization, according to an exemplary embodiment.

Referring now to FIG. 5, a flowchart illustrating a method 600 for animal production optimization is shown, according to an exemplary embodiment. Method 600 generally includes identifying optimized values for one or more animal information inputs according to at least one optimization criteria. Although the description of method 600 includes specific steps and a specific ordering of steps, it is important to note that more, fewer, and/or different orderings of the steps may be performed to implement the functions described herein. Further, implementation of a step may require reimplementation of an earlier step. Accordingly, although the steps are shown in a linear fashion for clarity, several loop back conditions may exist.

In a step 605, enterprise supervisor 200 is configured to receive the animal information inputs. The animal information inputs can be received from a user through user interface 210, populated automatically based on related data, populated based on stored data related to the user, or received in a batch upload from the user. The received animal information inputs include a designation of one or more of the animal information inputs as a variable input. The designation as a variable input may be received for single, multiple, or all of the animal information inputs.

In a step 610, enterprise supervisor 200 is configured to receive an optimization criteria through user interface 210 or, alternatively, receive a preprogrammed optimization criteria. The optimization criteria may include maximizing productivity, reducing expenses, maximizing quality of output, achieving productivity targets, etc. In an exemplary embodiment, the optimization criteria may be an objective function requiring minimization or maximization. The objective function may have constraints incorporated therein or may be subject to independent constraints. The objective function may be a function of any combination of variables of the animal production system.

In a step 615, enterprise supervisor 200 is configured to communicate the animal information inputs and optimization criteria to simulator 300. Upon receiving the animal information inputs and optimization criteria, simulator 300 is configured to generate a set of animal requirements in a step 620.

In a step 625, the set of animal requirements are communicated from simulator 300 through enterprise supervisor 200 to formulator 500. Formulator 500 is configured to generate a least cost animal feed formulation based upon the animal requirements and nutrient information received from nutrient engine 450 in a step 630. The least cost animal feed formulation may be determined based at least in part on the components within the animals environment, represented by third ingredient listing 430.

In a step 635, enterprise supervisor 200 is configured to generate optimized values for the one or more variable inputs received in step 605, as discussed in detail above with reference to FIG. 2.

Although specific functions are described herein as being associated with specific components of system 100, functions may alternatively be associated with any other component of system 100. For example, user interface 210 may alternatively be associated with simulator 300 according to an alternative embodiment.

Many other changes and modifications may be made to the present invention without departing from the spirit thereof. The scope of these and other changes will become apparent from the appended claims.

What is claimed is:

1. A system for generating an animal feed formulation for an animal based on environmental nutrient inputs, comprising:
   a central processing unit coupled to a memory, the central processing unit running one or more programs, at least one of the programs comprising,
   (i) a simulator engine configured to generate a set of animal requirements in view of environmental nutrients received by the animal based on characteristics of the animal wherein the environmental nutrients comprise one or more nutrients that are received and/or utilized by the animal that are not fed to the animal; and
   (ii) a formulator engine configured to receive the set of animal requirements and generate an optimized animal feed formulation from the animal requirements;
   wherein said animal feed formulation is communicated to a user interface.

2. The system of claim 1, wherein the simulator engine is further configured to project the environmental nutrients received by an animal based on a listing of environmental ingredients available to the animal and the characteristics of the animal.

3. The system of claim 1, further including an enterprise supervisor engine configured to generate an optimized value for at least one variable input that is varied by the system to generate a value, the variable input having an effect on the environmental nutrients received by the animal.

4. The system of claim 3, wherein generating an optimized value for the at least one variable input includes providing a projected effect of a modification to the at least one variable input.

5. The system of claim 1, wherein the simulator engine is further configured to generate a projected effect of consumption of the environmental nutrients by the animal.

6. The system of claim 5, wherein the projected effect is the effect of a waste stream generated by the animal on the environmental nutrients.

7. The system of claim 5, further including an enterprise supervisor engine configured to generate an optimized value for at least one variable input that is varied by the system to generate a value, the optimized value being configured to minimize a detrimental effect of the environmental nutrients received by an animal.

8. The system of claim 1, further including an environmental ingredient performance simulator configured to generate an environmental ingredient performance profile based upon consumption of environmental ingredients and the inputs provided to the environment.

9. A method for generating an animal feed formulation for an animal based on environmental nutrient inputs, the method comprising:
   receiving a listing of environmental nutrient inputs wherein the environmental nutrient inputs comprise one or more nutrients that are received and/or utilized by the animal that are not fed to the animal;
   generating a projection of consumption of the environmental nutrient inputs by the animal;
   determining a set of animal nutritional requirements for the animal in view of the consumption of the environmental nutrient inputs by the animal based on the characteristics of the animal;
   generating an optimized animal feed formulation based on the animal nutritional requirements; and
   communicating the animal feed formulation to a user interface;

wherein the method is implemented with one or more processors.

10. The method of claim 9, further including generating an optimized value for at least one variable input that is varied in the method to generate a value, the variable input having an effect on the environmental nutrient inputs received by the animal.

11. The method of claim 10, wherein generating an optimized value for the at least one variable input includes providing a projected effect of a modification to the at least one variable input.

12. The method of claim 9, further including generating a projected effect of the consumption of the environmental nutrient inputs by the animal.

13. The method of claim 12, wherein the projected effect is the effect of a waste stream generated by the animal on the environmental nutrient inputs.

14. The method of claim 12, further including generating an optimized value for at least one variable input, the optimized value being configured to minimize a detrimental effect of the environmental nutrient inputs received by an animal.

15. The method of claim 9, further including generating an environmental ingredient performance profile based upon the consumption of environmental ingredients and inputs provided to the environment.

16. A system for generating an animal feed formulation for an animal, comprising:
   a central processing unit coupled to a memory, the central processing unit running one or more programs, at least one of the programs comprising,
   (i) a simulator engine configured to receive a plurality of animal information inputs and generate animal requirements based on the animal information inputs, the animal information inputs including a listing of environmental ingredients comprising environmental nutrients that are available to the animal, wherein at least one of the animal information inputs is designated as a variable input that is varied by the system to generate a value and wherein the environmental ingredients comprise one or more nutrients that are received and/or utilized by the animal that are not fed to the animal;
   (ii) a formulator engine, the formulator engine configured to receive a plurality of animal feed ingredient inputs and generate an animal feed formulation composed of the animal feed ingredients based on the animal requirements and projected consumption of the environmental ingredients by the animal; and
   (iii) an enterprise supervisor engine configured to optimize the animal feed formulation according to at least one optimization criteria, and further configured to generate an optimized value for the at least one variable input based on the at least one optimization criteria;
   wherein the animal feed formulation is communicated to a user interface.

17. The system of claim 16, wherein the simulator engine is further configured to generate a projection of environmental nutrients received by an animal based on a listing of environmental ingredients available to the animal and characteristics of the animal.

18. The system of claim 16, wherein the enterprise supervisor engine is further configured to generate an optimized value for at least one variable input, the variable input having an effect on environmental nutrients received by an animal.

19. The system of claim 18, wherein generating an optimized value for the at least one variable input includes providing a projected effect of a modification to the at least one variable input.

20. The system of claim 16, wherein the simulator engine is further configured to generate a projected effect of the consumption of the environmental ingredients by the animal.

21. The system of claim 20, wherein the projected effect is the effect of a waste stream generated by the animal on the environmental ingredients.

22. The system of claim 20, wherein the enterprise supervisor engine is further configured to generate an optimized value for at least one variable input, the optimized value being configured to minimize a detrimental effect of environmental nutrients received by an animal.

23. The system of claim 16, wherein the simulator engine includes an environmental ingredient performance simulator configured to generate an environmental ingredient performance profile based upon the consumption of the environmental ingredients and inputs provided to the environment.

* * * * *

UNITED STATES PATENT AND TRADEMARK OFFICE
CERTIFICATE OF CORRECTION

| | | |
|---|---|---|
| PATENT NO. | : 7,827,015 B2 | Page 1 of 1 |
| APPLICATION NO. | : 11/191255 | |
| DATED | : November 2, 2010 | |
| INVENTOR(S) | : Bruce Brim McGoogan et al. | |

It is certified that error appears in the above-identified patent and that said Letters Patent is hereby corrected as shown below:

In column 16, line 19, delete "216" and insert -- 210 --, therefor.

In column 30, line 5, delete "ray" and insert -- may --, therefor.

In column 36, line 11, in Claim 1, after "animal" insert -- , --.

In column 36, line 54, in Claim 9, after "inputs" insert -- , --.

Signed and Sealed this
Twenty-second Day of February, 2011

David J. Kappos
*Director of the United States Patent and Trademark Office*